US012109165B2

(12) United States Patent
Hart et al.

(10) Patent No.: US 12,109,165 B2
(45) Date of Patent: Oct. 8, 2024

(54) PERCUSSION MASSAGER HAVING A TEMPERATURE-CONTROLLED MASSAGE NODE

(71) Applicant: Merchsource, LLC, Irvine, CA (US)

(72) Inventors: Rene Jon Hart, New Canaan, CT (US); Keith Lawrence Covey, Costa Mesa, CA (US); Adam Sbeglia, Fullerton, CA (US); David Yang, Santa Ana, CA (US); Denny Szupao Liao, Tustin, CA (US)

(73) Assignee: MerchSource, LLC, Irvine, CA (US)

(*) Notice: Subject to any disclaimer, the term of this patent is extended or adjusted under 35 U.S.C. 154(b) by 0 days.

(21) Appl. No.: 17/567,284

(22) Filed: Jan. 3, 2022

(65) Prior Publication Data

US 2022/0362097 A1 Nov. 17, 2022

Related U.S. Application Data

(60) Provisional application No. 63/247,334, filed on Sep. 23, 2021, provisional application No. 63/189,240, filed on May 17, 2021.

(51) Int. Cl.
*A61H 23/00* (2006.01)
*A61F 7/00* (2006.01)

(52) U.S. Cl.
CPC ........... *A61H 23/006* (2013.01); *A61F 7/007* (2013.01); *A61F 2007/0073* (2013.01);
(Continued)

(58) Field of Classification Search
CPC .................................................... A61H 23/06
See application file for complete search history.

(56) References Cited

U.S. PATENT DOCUMENTS

| 5,097,828 A | 3/1992 | Deutsch |
| 6,089,664 A | 7/2000 | Yoshida |

(Continued)

FOREIGN PATENT DOCUMENTS

| CN | 201150633 Y | 11/2008 |
| CN | 201267597 | 7/2009 |

(Continued)

OTHER PUBLICATIONS

Amazon "HoMedics Percussion Pro Handheld Massager with Heat" (2018). (Year: 2018).*

(Continued)

*Primary Examiner* — Bradley H Philips
*Assistant Examiner* — Savannah L Gabriel
(74) *Attorney, Agent, or Firm* — Avyno Law. P.C.

(57) ABSTRACT

A temperature-controlled massage node that imparts either or both a heating or cooling effects is provided, which may be attached to a massager to impart a heating or cooling effect on a user with a massage effect, or optionally, without a massage effect. The temperature-controlled massage node may be affixed to the massager or may be removably coupled. The temperature-controlled massage node may be powered by the same power source as the massager or may include an independent power source located, for example, in the massage node. The massage node may be used with a massager that provides percussive massage effects, such as a massage gun, or may be used with a vibrating massager. Optionally, the massage node may include independent power, a controller and a motor to supply both a vibrating massage effect and hot and cold effect, either alone or in combination.

29 Claims, 19 Drawing Sheets

(52) U.S. Cl.
CPC ............... *A61F 2007/0075* (2013.01); *A61F 2007/0078* (2013.01); *A61F 2007/0087* (2013.01); *A61H 2201/0157* (2013.01); *A61H 2201/0207* (2013.01); *A61H 2201/0214* (2013.01); *A61H 2201/0235* (2013.01); *A61H 2201/0285* (2013.01); *A61H 2201/5043* (2013.01)

(56) References Cited

U.S. PATENT DOCUMENTS

| | | | |
|---|---|---|---|
| 6,241,027 | B1 | 6/2001 | Beck et al. |
| 6,432,072 | B1 | 8/2002 | Harris et al. |
| 6,682,496 | B1 | 1/2004 | Pivaroff |
| 7,273,159 | B2 | 9/2007 | Brotto |
| 7,384,405 | B2 | 6/2008 | Rhoades |
| 8,713,739 | B1 | 5/2014 | Alas et al. |
| 9,089,470 | B2 | 7/2015 | Lev et al. |
| 10,314,762 | B1 | 6/2019 | Marton et al. |
| 10,993,874 | B1 * | 5/2021 | Marton .................... A61H 1/00 |
| 2001/0007952 | A1 | 7/2001 | Shimizu |
| 2002/0167791 | A1 | 11/2002 | Goris |
| 2002/0177795 | A1 * | 11/2002 | Frye ....................... A61H 1/008 601/84 |
| 2003/0229300 | A1 | 12/2003 | Winkley |
| 2005/0020947 | A1 | 1/2005 | Dehli |
| 2005/0203445 | A1 | 9/2005 | Tsai |
| 2005/0209537 | A1 * | 9/2005 | Gleason ............. A61H 23/0263 601/72 |
| 2005/0209539 | A1 | 9/2005 | Lev et al. |
| 2006/0058714 | A1 | 3/2006 | Rhoades |
| 2008/0014011 | A1 | 1/2008 | Rossen |
| 2008/0119767 | A1 * | 5/2008 | Berry .................... A61H 21/00 601/46 |
| 2008/0300529 | A1 | 12/2008 | Reinstein |
| 2010/0274162 | A1 | 10/2010 | Evans |
| 2013/0046212 | A1 | 2/2013 | Nichols |
| 2014/0276255 | A1 | 9/2014 | McGushion |
| 2014/0378555 | A1 | 12/2014 | Hung et al. |
| 2015/0005682 | A1 | 1/2015 | Danby et al. |
| 2015/0121900 | A1 | 5/2015 | Yamazaki |
| 2015/0182290 | A1 | 7/2015 | Grez |
| 2015/0297393 | A1 | 10/2015 | McGushion |
| 2015/0305969 | A1 | 10/2015 | Giraud et al. |
| 2016/0089537 | A1 | 3/2016 | Yamazaki |
| 2016/0151238 | A1 | 6/2016 | Crunick et al. |
| 2016/0331308 | A1 | 11/2016 | Zhou |
| 2016/0367425 | A1 | 12/2016 | Wersland |
| 2017/0304145 | A1 | 10/2017 | Pepe |
| 2018/0185236 | A1 | 7/2018 | Levi |
| 2018/0200141 | A1 | 7/2018 | Wersland et al. |
| 2018/0228691 | A1 | 8/2018 | Marton et al. |
| 2018/0263845 | A1 | 9/2018 | Wersland et al. |
| 2018/0280675 | A1 * | 10/2018 | Tharp ..................... A61M 5/32 |
| 2019/0015294 | A1 | 1/2019 | Nazarian et al. |
| 2019/0015295 | A1 | 1/2019 | Marton et al. |
| 2019/0060115 | A1 | 2/2019 | Novkov et al. |
| 2019/0136889 | A1 | 5/2019 | Wersland et al. |
| 2019/0159961 | A1 | 5/2019 | Chuang |
| 2019/0175434 | A1 * | 6/2019 | Zhang ................ A61H 15/0085 |
| 2020/0155410 | A1 | 5/2020 | Smith, Jr. et al. |
| 2020/0268594 | A1 * | 8/2020 | Pepe .................. A61H 15/0085 |
| 2020/0289161 | A1 | 9/2020 | Scooros |
| 2021/0077340 | A1 | 3/2021 | Pepe |
| 2021/0128402 | A1 * | 5/2021 | Dai ......................... A61H 1/00 |
| 2021/0145539 | A1 | 5/2021 | Greve |
| 2021/0244611 | A1 * | 8/2021 | Wersland ............. A61H 23/006 |
| 2021/0401663 | A1 * | 12/2021 | Wersland ............... A61N 1/328 |
| 2022/0040030 | A1 * | 2/2022 | Tang ................... A61N 5/0625 |
| 2022/0117073 | A1 | 4/2022 | Wandke et al. |
| 2022/0168175 | A1 * | 6/2022 | Tang ........................ H01B 7/22 |
| 2022/0233397 | A1 | 7/2022 | Huang |

FOREIGN PATENT DOCUMENTS

| | | | |
|---|---|---|---|
| CN | 110025466 | A | 7/2019 |
| CN | 211095853 | | 7/2020 |
| JP | 6096570 | B2 | 3/2017 |
| KR | 100539364 | B1 | 1/2006 |
| KR | 100746214 | B1 | 8/2007 |
| KR | 101578689 | B1 | 12/2015 |
| KR | 2017098577 | | 8/2017 |
| KR | 1020170098577 | A | 8/2017 |
| KR | 2020170003668 | U | 10/2017 |
| KR | 101810511 | B1 | 12/2017 |
| TW | M572227 | U | 1/2019 |
| WO | 2014147855 | A1 | 9/2014 |

OTHER PUBLICATIONS

Memmert, "Advanced Peltier Technology", Jul. 5, 2017. (Year: 2017).*
HoMedics website; Thera-P Hot & Cold Massager (2022); https://www.homedics.com/thera-p-hot-cold-massager/.
Machine translation of KR-10-20170098577 (Year:2017).

* cited by examiner

PERCUSSION MASSAGER HAVING A TEMPERATURE-CONTROLLED MASSAGE NODE

CROSS REFERENCE TO RELATED APPLICATIONS

This application claims priority to U.S. Provisional Patent Application Ser. No. 63/189,240, filed on May 17, 2021, titled Percussion Massager Having a Temperature-Controlled Massage Node and U.S. Provisional Patent Application Ser. No. 63/247,334, filed on Sep. 23, 2021, titled Percussion Massager Having a Temperature-Controlled Massage Node, both applications of which are incorporated herein by reference in their entirety.

FIELD OF INVENTION

The invention relates to a temperature-controlled massage node and, in particular, to a temperature-controlled massage node that is able to impart heating and cooling effects on a user and that may be adapted for use with a percussion massager.

BACKGROUND

Percussion massagers are becoming increasingly popular among consumers for muscle recovery, and for use in a variety of personal, professional and/or medical treatments, including, but not limited to, massage therapists, physical therapists and chiropractic treatments. Percussion massagers need to be powerful enough to reach the deepest layers of one's muscles, and target knots and sore muscles to provide a deep tissue massage experience. Percussion massagers may be offered for sale in the form of massage guns, which are powerful handheld massagers that include a piston that provides rapid, percussive tapping. Such massage guns generally come with different piston attachments for imparting different massage effects.

Percussive massage is generally used for more aggressive treatment to target sore and tight muscle groups. When treating sore muscles, the use of heat and/or ice is generally also applied to help increase blood flow, loosen tight muscles and, in the case of ice, to reduce inflammation.

Commercially available percussion massagers generally include, for example, an electric motor that drives a reciprocating piston within a housing. Massage nodes or massage heads are generally then attached to the piston to provide different percussive massage effects. Given the benefits of imparting heating and cooling effects on a user to help treat tight and sore muscles, a user would greatly benefit from a massage node that is able to impart heating and cooling effects on a user and that may be adapted to for use with a percussion massager. In particular, as explained further below, a massage node may be provided that is affixed or removably coupled to a handle or percussion massager that is able to impart a heating or cooling effect to a user through the use of a temperature-controlled massage node, either together or separate from a percussion massage effect.

SUMMARY

A temperature-controlled massage node that imparts either or both a heating or cooling effect is provided for use, for example, with a portable handheld massager. When used with a massager, the temperature-controlled massage node may be used with a massage effect, or optionally, without the percussive massage effect.

The temperature-controlled massage node may be affixed to a massager or may be removably coupled to the massager housing. Optionally, the temperature-controlled massage node may be affixed to a handle that provides power to the temperature-control massage node without providing massage effects. For example, the handle may maintain the node in a stationary position or may optionally vibrate the node.

The temperature-controlled massage node may be comprised of a node housing having an upper portion and lower portion having at least one electrical contact on the lower portion of the housing. A heating element is positioned within the node housing in communication with the at least one electrical contact, and a contact medium is positioned on the upper portion of the massage node above the heating element. The heating element may be a Peltier plate that is able to both heat and cool the massage node. The node may further include a temperature sensor, heat dissipating device and/or fan. Optionally, the housing may include perforations for dissipating heat from the node. The contact medium may be a hard or soft thermal conductive material.

The temperature-controlled massage node may be powered by the same power source as the massager or may include an independent power source, such as a battery, located in the massage node. In this regard, the heating element positioned within the node will be in electrical communication with the battery in the node for powering the heating element. With the battery in the node, other component parts that may be included in the nodes, such as a temperature sensor or fan may also be in communication with and powered by the battery in the massage housing. In all examples, the temperature sensor may be a thermocouple or thermistor. Further, a heat sink may be included in the housing or incorporated into, or made part of, the node housing. When a battery is included on the node, electrical contacts, wireless charging, or a plug receptacle is provided to recharge the battery within the housing.

When the temperature-controlled massage node is design for removably coupling to a massager or a handle, the temperature-controlled massage node may include a node housing having an upper portion and lower portion with a contact medium positioned on the upper portion of the massage node and at least one mounting sleeve or shaft on the lower portion of the node for removably coupling the massage node to a massager or handle. If power for the node is to be drawn from the massager or handle, the mounting sleeve or shaft may further include a plate having electrical contacts for powering the heating element, or Peltier plate, positioned within the node housing. The temperature-controlled massage node may further include either or both a fan and heat dissipating device, such as a heat sink, within the node housing. When a fan is included, the fan will also be in communication with the electrical contacts to power the fan.

In another example, a portable percussion massager is provided that includes a housing, having a motor within the housing driving a piston. At least one temperature-controlled massage node is then attached to the piston, either directly or indirectly, that includes a Peltier plate to heat and cool the massage node. The massage node may be affixed or removably coupled to the piston. If removably coupled, the massage node may include first electric contacts and the housing may include a node mount having second electrical contacts for coupling with the first electrical contacts on the massage node. The housing may include a power source, such as a battery, and the both the massage node and motor may be electrically connected to the same power source.

The portable percussion massager may also comprise a housing having a motor positioned within the housing, where the motor has a shaft connected to a crankshaft. A rod is then connected at its first end to the crankshaft at a point that is offset from the rotational axis of the crankshaft. A piston is then coupled to a second end of the rod, opposite the crankshaft. A temperature-controlled massage node is then coupled to the piston at its end opposite attachment to the rod. The temperature-controlled massage node includes a node housing, a heat dissipation or absorption device, a Peltier plate and a contact medium for covering the Peltier plate to prevent direct contact by a user with the Peltier plate. The temperature-controlled massage node may be heated to a predetermined temperature upon activation of the Peltier plate, and may include, in some examples, allowing the user to heat or cool the Peltier plate to at least one, two or three predetermined temperatures. Like in other examples, the temperature-controlled massage node may be removably coupled to the piston. When removably coupled, the massage node includes first electrical contacts. The massager housing includes a node mount having second electrical contacts for pairing with the first electrical contacts on the massage node. Here, the massage node and motor can be electrically connected to the same power source, which may be a battery positioned in the housing or handle of the massager.

In another example, a massager is provided that comprises a housing and at least one temperature-controlled massage node coupled to the housing, the temperature-controlled massage node includes a Peltier plate for imparting heat or cold on the massage node. A motor is contained within the housing for imparting a massage effect on the at least one temperature-controlled massage node. The massager further includes an annular light ring having at least one LED mounted thereon for illuminating in a first state when the Peltier plate is heating the node and a second state when the Peltier plate is cooling the node. The annular light ring may be positioned on either the massage node or the massage housing.

The motor may impart a vibrating massage effect on the massage node. Alternatively, or in addition thereto, the motor may include a shaft with a crankshaft attached thereto. A rod is then attached to the crankshaft within a piston coupled to the end of the rod opposite the crankshaft. The temperature-controlled massage node is then coupled to the piston for moving the massage node in a percussive manner.

Like with other examples, the temperature-controlled massage node may be removably coupled to the piston and may be heated to a predetermined temperature upon activation of the Peltier plate. The massage node may include first electrical contacts and the massage housing may include a node mount for removably coupling the massage node to the massage housing. The node mount having second electrical contacts for aligning with the first electrical contacts on the massage node.

A temperature-controlled massage node is further provided that may comprise a node housing having an upper portion and lower portion, a heating element positioned within the housing, and a contact medium positioned above the heating element on the upper portion of the node housing. The node further includes an indication display including at least one LED positioned on a mounting surface, where the indication display illuminates light in a first state when the heating element is off and a second state when the heating element is on. The temperature-controlled massage node may be a Peltier plate that both heats and cools the massage node.

In yet another example, a massager is provided having a temperature-controlled massage node that includes a massager housing and massage node, where the massage node includes a node housing having an upper portion and lower portion with at least one electrical contact on the lower portion of the housing. The massage node further includes a heating element positioned within the node housing in communication with the at least one electrical contact and a contact medium positioned above the heating element on the upper portion of the node housing. In this example, the massager further includes an indication display including at least one LED positioned on a mounting surface, where the indication display illuminates light in a first state when the heating element is on. The indication display may be a light ring coupled to the massage node housing and including at least one LED positioned on a mounting surface of the light ring, where the light ring illuminates light in a first state to indicate that the heating element is producing heat.

In still another example, a massager having a temperature-controlled massage node is provided, where the massager includes a massager housing and a massage node attached to the massager housing. The massage node includes a node housing having an upper portion and lower portion with a contact medium positioned on the upper portion of the node housing. A Peltier plate is positioned within the node housing below the contact medium for heating and cooling the contact medium. The massager in this example may further include an indication display that is a light transmissive ring. The indication display includes at least one LED positioned on a mounting surface, where the indication display illuminates light in a first color when the Peltier plate is heating the contacting plate and a second color when the Peltier plate is cooling the contact medium. Here, the light ring can be positioned on either the massager housing or the massage node.

In all of the above examples that includes heating elements or indication displays, the heating element may be a Peltier plate that both heats and cools the massage node. The indication display may be a light right that includes a plurality of LEDs that illuminates in a first, second, third, or n+1 state or in a first, second, third, or n+1 color, where the LEDs are single color, dual color, or multicolor LEDs electrically connected in parallel or in series and mounted on a ring mount having a mounting surface. The states or colors of the LEDs can indicate that the Peltier plate is off, is heating, or is cooling. The states or colors can vary in light effects and intensity and can be a solid state or a varying state. For example, at least one LED can illuminate in one state when the Peltier plate is heating the node or contact medium and another state when the Peltier plate is cooling the node or contact medium. Additionally, the at least one LED can illuminate in another state when the Peltier plate is off, which can include not illuminating any LEDs. When the indication display includes a plurality of LEDs, the plurality of LEDs may include a first set of LEDs illuminating in one color and a second set of LEDs illuminating in another color, where the plurality of LEDs illuminates the indication display in one state or color when the Peltier plate is heating the node or the contract medium and another state or color when the Peltier plate is cooling the node or contact medium. The illumination states or color can, for example, be the indication display illuminating a shade of red (e.g., when heating) or a shade of blue (e.g., when cooling).

In all the above examples, the massage node may include a heat dissipating device, which may be a heat sink, made, for example of metal, or a fan for active cooling, or both. The contact medium may be, for example, be an aluminum or stainless-steel plate (or other thermal conductive plate) and may be formed as part of the contact node housing or be a separate piece. Optionally, a softer material may be used in connection with the thermal conductive plate or in place of the thermal conductive plate, such as a thermal conductive cloth like pad or material, which may be made, for example, from cloth, plastic, graphite, carbon fiber and/or a silicon material (such as a gel or resin) having conductive fibers, to name a few examples.

A thermal conductor, such as a thermal paste, may be positioned between the Peltier plate and the contact media to transfer heat and/or cold between the Peltier plate and the contact medium. The Peltier plate may be, for example, a single Peltier chip with reverse polarity for heating and cooling. While the illustrated examples show the use of only one single Peltier plate or chip, more than one plate or chip may also be utilized in different configurations, such as by stacking the chips or positioning the chip side-by-side. The temperature-controlled massage node may be affixed to the piston or, alternatively may be removably coupled.

To power the Peltier plate when the massage node is affixed to the massager housing or body, flexible wiring may extend from the power source in the housing through the piston to connect to electrical contacts in communication with the Peltier plate. When the massage node is removably coupled to the piston, the electrical contacts in communication with the Peltier plate may be electrical contact pins, plates, rings or pin receptacles that contact corresponding electrical contact pins, plate, leaf spring plate, or ring to close the circuit and provide power to the Peltier plate for operation.

The temperature-controlled massage node may operate over a range of temperatures between hot and cold, operate at a consistent single hot temperature—or a consistent single cool temperature, or at both consistent single hot and cold temperatures. For example, the temperature-controlled massage nodes may operate over a select preset number of temperatures that may be user selected on the location of the body of the massager or may be operated only at a single heat setting and/or a single cool setting (or both). While the Peltier plate may provide both heating and cooling features, the temperature-controlled massage node of the present invention may utilize only one of the heating and cooling features rather than both. The heating and cooling features may also be offered separate from or only in conjunction with the operation of the percussion massage feature of the percussion massager.

Other devices, apparatus, systems, methods, features and advantages of the invention are or will become apparent to one with skill in the art upon examination of the following figures and detailed description. It is intended that all such additional systems, methods, features and advantages be included within this description, be within the scope of the invention, and be protected by the accompanying claims.

DESCRIPTION OF FIGURES

The invention may be better understood by referring to the following figures. The components in the figures are not necessarily to scale, emphasis instead being placed upon illustrating the principles of the invention.

FIG. 9A illustrates an exploded view of the light ring of FIG. 9.

DETAILED DESCRIPTION OF THE INVENTION

Figure 1:
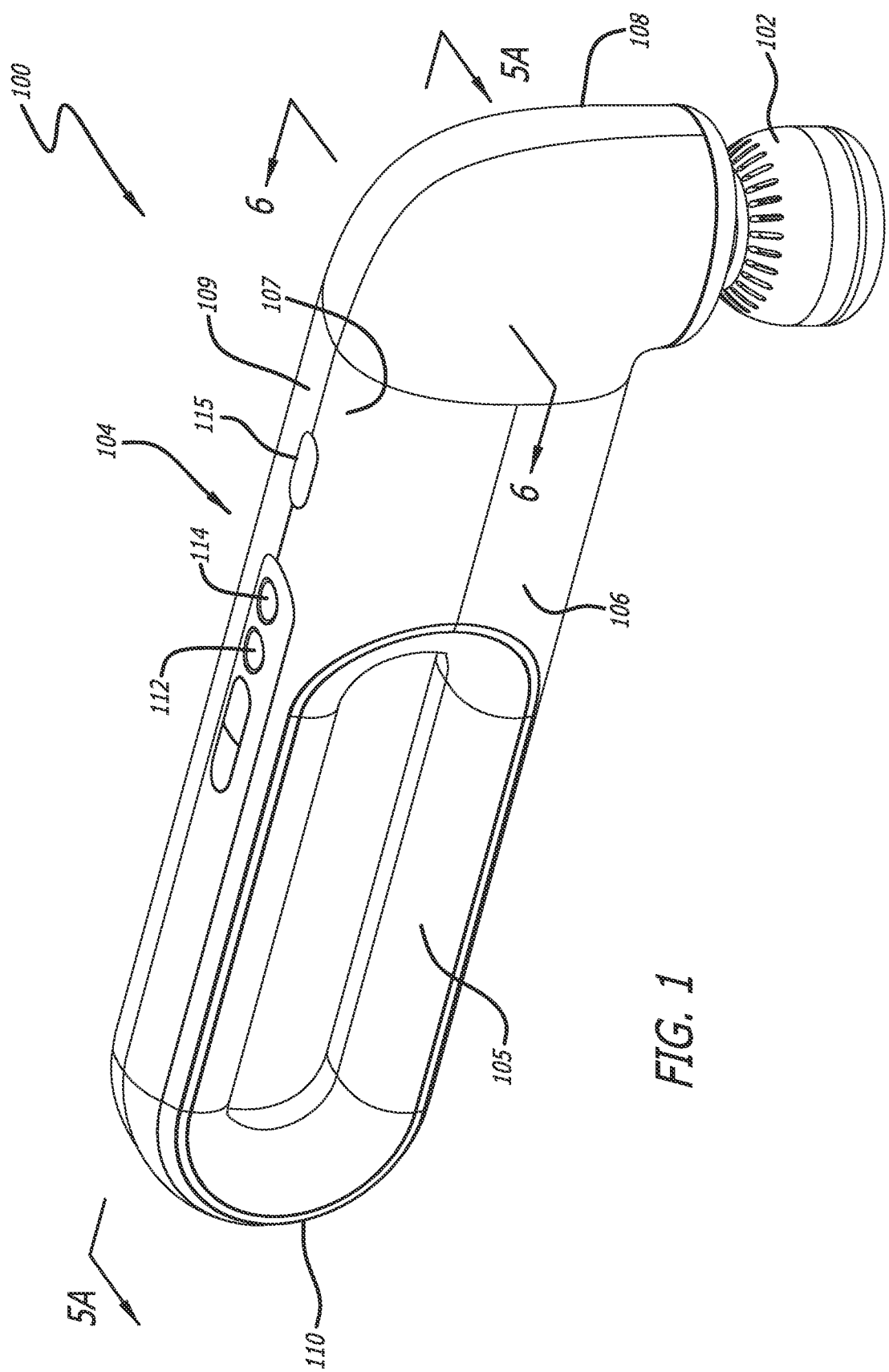
FIG. 1 illustrates a top side perspective view of one example of an implementation of a portable handheld percussion massager of the present invention.

FIGS. 1-20 illustrate several examples of different implementations of a portable handheld percussion massager of the present invention that includes a temperature-controlled massage node which, as illustrated in FIGS. 1-6, may be affixed to the percussion massager, or may be removably attached, as illustrated in FIGS. 7-17. Further, the temperature-controlled massage node may be powered by the same power source as the percussion massager or may include an independent power source located, for example, in the massage node. In all examples, the temperature-controlled massage node of the present invention is designed to impart either or both a heating or cooling effect to different locations of a user's body with the percussive massage effect, or optionally, without the percussive massage effect.

For purposes of this application, when the node is referred to as "affixed" to the percussion massager, it means that the node is not intended to be a removable attachment. While the node may be permanently attached or physically removably (in that the node is a separate piece from the massager), when a node is deem affixed to the percussion massager, it is connected to the massager in a manner not intended to be removable by the user. In other words, an affixed node is distinguishable from a removably attached or removeable coupled node; however, both removably attached nodes and affixed nodes are attached to the percussion massager for use.

While the examples illustrated in FIGS. 1-19 show a portable hand-held massager using a motor, with a percussion assembly, to impart a percussive massage effect on the massage node, it is recognized that the present invention may be embodied in any type or shape of massager, including those imparting only vibration upon the user. For example, the present invention may be used in a massager taking the form of a massage gun, which is typically recognized as a piston, attached to a rod and crankshaft, all driving by a motor, that provides rapid, percussive tapping, which gun may include different piston attachments for imparting different massage effects. The present invention may also take the form of a wand-type massager or other hand-held massage apparatus that may impart, for example, only a vibrating massage effect, with either a removable massage node or affixed massage node.

The massage nodes referenced throughout this specification are referred to as "temperature-controlled" massage node. "Temperature-controlled" as used in this specification shall mean a massage node that is able to operate at different temperatures than ambient temperature. For example, a "temperature-controlled" massage node may be a massage node that is able to be either or both heated or cooled, each at a single temperature, or alternatively at a range of temperatures.

While the examples below discuss the inclusion of a thermoelectric heater/cooler, such as a Peltier plate, to vary the temperature imparted by the massage node on the user, a heat element or cooling element could be provided in place of the thermoelectric heater/cooler, such that the massage node of the present invention only imparts heat or cold effects on the user (but not both). In this regard, heating elements, such as heating films or heating plates can be used in place of the Peltier plate to impart heating effects on a user. Additionally, if only heating or cooling is desired for a particular application, a Peltier plate may still be used, by providing for the current to flow through the Peltier plate in only one direction.

Further, while the percussion massager of the present invention is referenced throughout the specification in a single orientation, it should be understood that the percussion massager described herein can be used in various orientations and is not limited to use in the orientations illustrated in the drawings and described in the specification. Direction terms are used only with respect to the orientation of the percussion massager as illustrated in the drawings.

FIG. 1-6 illustrate one example implementation of a portable handheld percussion massager 100 of the present invention that includes a temperature-controlled massage node 102 that, in this example, is affixed to the percussion massager 100. As illustrated in FIG. 1, which is a top side perspective view of a portable handheld percussion massager 100, the portable percussion massager 100 includes a massager housing 104, which includes central housing 106, forward housing 108, and rearward housing 110. In this example, the central housing 106, forward housing 108 and rearward housing 110 may be three separate pieces, with the central housing 106 and forward housing 108 each having right 107 and left 109 side panels that engage with one another to form a hollow massager housing 104. It should be understood, however, that the massager housing 104 may be made from any number of different pieces formed together or separately.

Also illustrated in FIG. 1, the percussion massager 100 includes a handle 105 which may be formed as part of the central and rearward housing 106, 110 as illustrated, or may be a separate piece extending from the massager housing 104 (as shown in FIGS. 7-17). In alternative implementations, the housing 104 may form a handle 105. Positioned on the massager housing 104 are controls 112 and 114, which allow the user to control the operation of the percussion massager 100. For example, the user may turn the percussion massager 100 on and off using user controls 112 and/or 114 or separate controls (not shown). The user can also use controls 112 and/or 114 to control the various speeds of the motor 202 (FIG. 2) to create different percussion massage effects and further control the hot and cold effects imparted by the temperature-controlled massage node 102 when the heating and cooing effects are engaged.

An indicator display having indicator light(s) 115 may also be provided on the massager housing 104 to communicate the state of the operation of the percussion massager 100 to the user. Indicator lights 115 may be one or more light emitting diode (LED) mounting on a mounting surface that illuminate, for example, when the massager is on. Indicator lights 115 may further be illuminated to indicate the speed of operation of the motor 202 of the percussion massager 100. Indicator lights 115 may also be illuminated to indicate whether the temperature-controlled massage mode 102 is operating, whether the temperature-controlled massage nodes 102 are operating in a heating mode or a cooling mode (e.g., a first hue or second hue, red or blue, or a shade of red/shade of blue), and/or at which preset temperature the temperature-controlled massage node 102 is operating.

Figure 2:
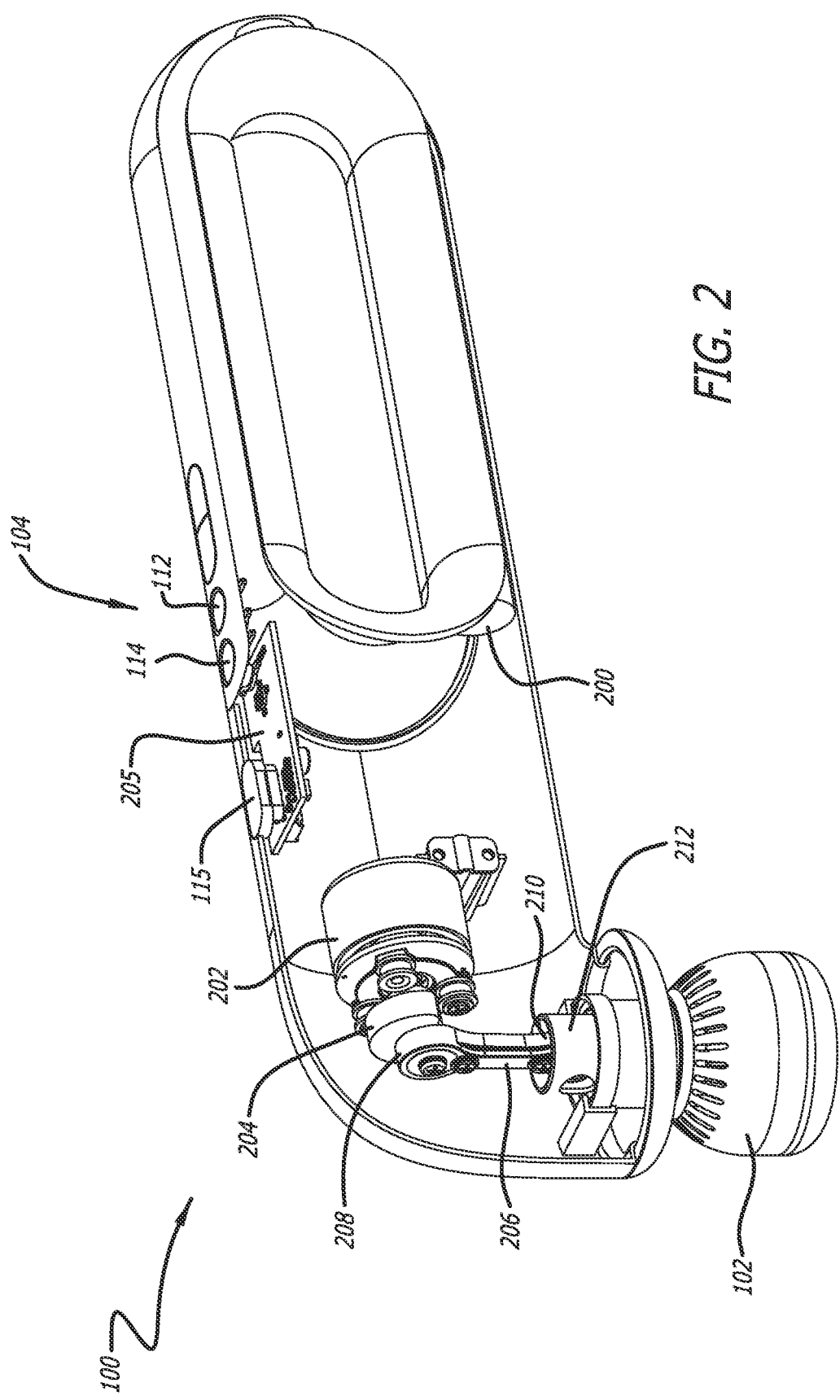
FIG. 2 illustrates a top side perspective view of the portable handheld percussion massager of FIG. 1 with the side panel of the massager housing removed.

FIG. 2 illustrates a top side perspective view of the portable handheld percussion massager 100 of the present invention with the side panel 109 of the central housing 106 and forward housing 108 (see FIG. 1) removed. Contained within the housing 104 is a power source 200, which in this case is a rechargeable battery, a motor 202 and a circuit board 205. The circuit board 205 operates as a controller for controlling the operation of the motor 202 and/or the heating and cooling effects of the temperature-controlled massage node 102. The circuit board 205 is in communication with, or electrically connected to, the power source 200. The battery 200 provides power to the circuit board, and may provide power directly to the motor, or indirectly to the motor through the circuit board, either of which provides the necessary power to the motor 202. The battery 200 may be comprised of lithium-ion battery cells connected in series to produce the voltage necessary to power the percussion massager 100, which may for example, consist of a series of cells producing approximately 25+ volts when fully charged. Such battery cells are commercially available from many different suppliers. The motor 202 may be a brushless DC electric motor having a shaft that rotates in response to electrical energy. The electric motor 202 may be, for example, a 24-volt brushless DC motor, of a type and brand a commercially available, or other type and sized motor suitable for the particular size and application of the portable massager 100.

Optionally, the power source 200 may be one or more batteries, one or more rechargeable batteries, and/or the percussion massager 100 and/or the massage node 102 may draw power through an external power source by, for example, plugging into a power outlet, such as a 110-volt outlet, to operate the massager 100, to recharge the batteries, or both. As stated before, the massage node 102 may draw power from the same power source as the massager 100 or may be powered independent from the massager 100 through one or more batteries, rechargeable batteries or through an external power source.

The motor 202 is provided to drive the temperature-controlled massage node 102 in a percussive motion. Alternatively, the motor 202 could be provided to impart only a vibrating massage effect, only a percussive massage effect or both. In the illustrated example, the motor 202 includes a crankshaft 204 that rotates about a central axis of the motor 202 via a motor shaft. A rod 206 having a first end 208 and second end 210 is then coupled at its first end 208 to the crankshaft 204 at a point offset from the rotational axis of the crankshaft 204. Attached to the second end 210 of the rod 206 is a piston 212 (or percussion driver), which has a temperature-controlled massage node 102 coupled to the piston 212 on its end 210 opposing the crankshaft 206.

Figure 3:
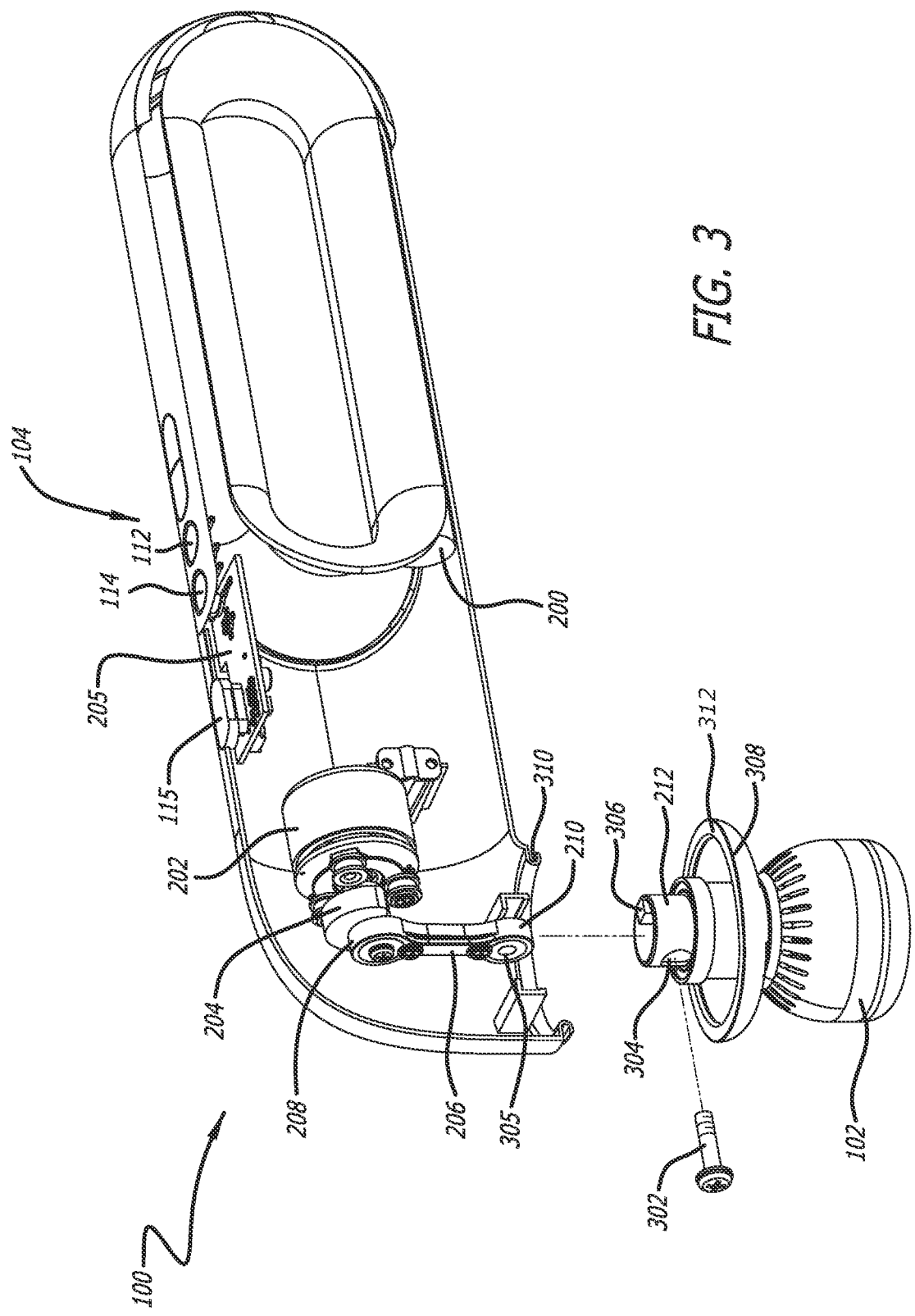
FIG. 3 illustrates a partially exploded perspective view of the portable handheld percussion massager of FIG. 2.

FIG. 3 illustrates a partially exploded perspective view of the portable handheld massager of FIG. 2. Here, the piston 212 and massage node 102 are shown removed from the rod 206. In this example, the piston 212 is attached to the second end 210 of the rod 206 with a screw 302 which is positioned through an opening 304 in the piston 212 and through a corresponding opening 305 on the second end 210 of the rod 206 when the rod 206 is inserted in the piston 212. Once through the opening 305 in the rod 206, the screw 302 is then secured against a brace 306 positioned against an interior wall of the piston 212. Despite being attached to the brace 306, the piston 212 remains generally hollow to allow for electrical wires to extend through the piston 212 to power the temperature-controlled massage node 102, and other possible components positioned with the massage node 102.

A flexible cover 308 is also provided above and around the massage node 102 (as oriented in FIG. 3) to close the massager housing 104 above the massage node 102. In this example, an interior edge 312 extending inward from the flexible cover 308 attaches to a perimeter channel 310 on the forward housing 108. The flexible cover 308 allows the piston 212 to move the massage node 102 up and down with the movement of the crankshaft 204 and rod 206 as they are driven by the motor 202 while allowing the massager housing 104 to remain closed.

Figure 4:
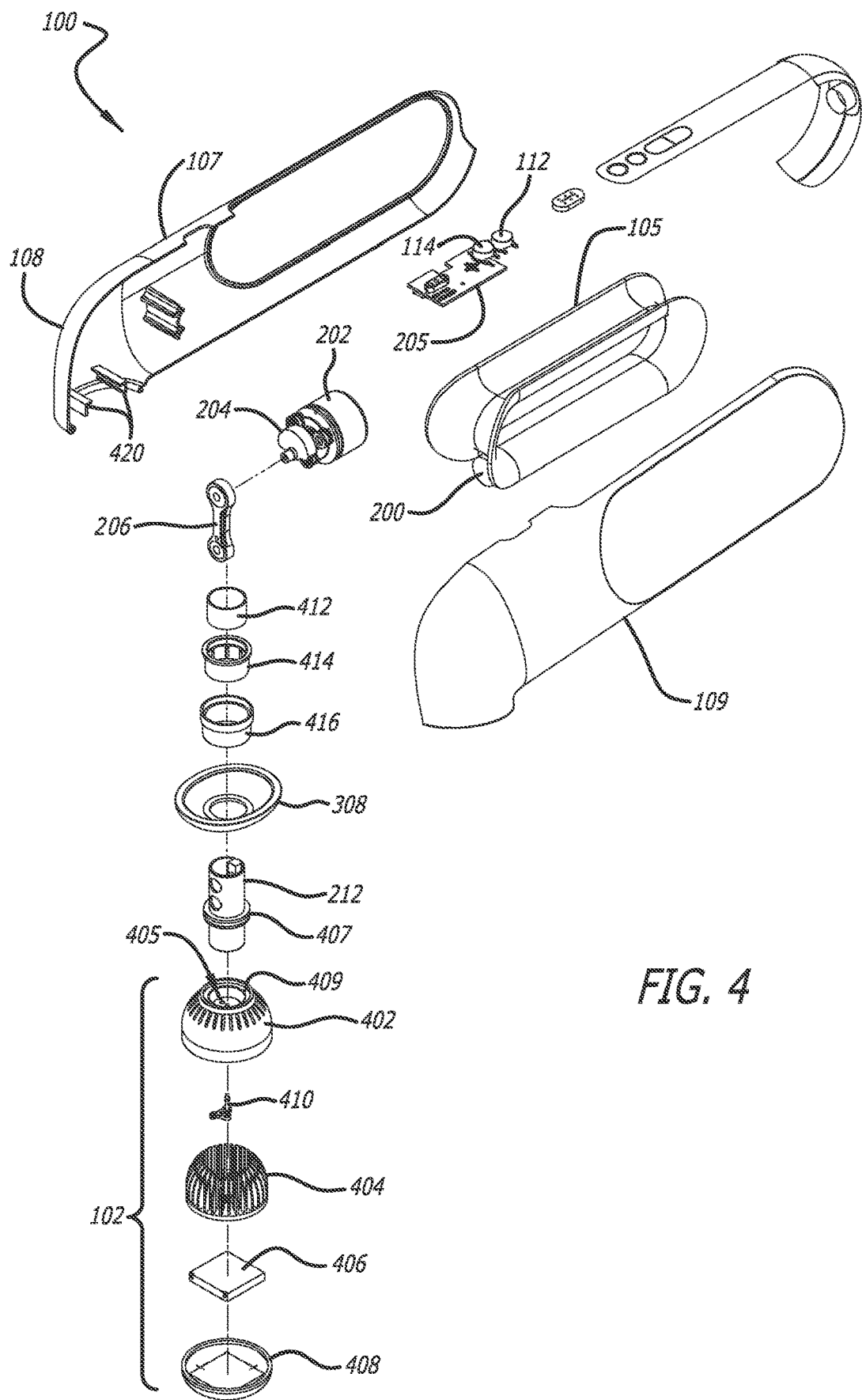
FIG. 4 illustrates an exploded perspective view of the portable handheld percussion massager of FIG. 1.

FIG. 4 illustrates an exploded perspective view of the portable handheld percussion massager 100 of FIG. 1. FIG. 4 best illustrates the component parts of the temperature-controlled massage node 102. Temperature-controlled massage node 102 includes a node housing 402, a heat dissipating or absorption device 404, and at least one thermoelectric heater/cooler 406, often referred to as a Peltier plate or chip, and a contact medium 408 for covering the Peltier plate 406 to help dissipate the heating and cooling effect of the Peltier plate 406 and transfer the heating or cooling effect to the user. The contact medium 408 may be, for example, be an aluminum or stainless-steel plate (or other thermal conductive metal) and may be formed as part of the node housing 402 or be a separate piece from the node housing 402. As set forth above, the contact medium 408 may include a softer material used in connection with the thermal conductive plate 408, for example as a cover, or alternatively, in place of the thermal conductive plate 408, such as a thermal conductive cloth-like pad or material, which may be made, for example, from cloth, plastic, graphite, carbon fiber and/or a silicon material (such as a gel or resin) having conductive fibers, to name a few examples.

The heat dissipating or absorption device 404 may be, as illustrated, a heat sink, which in this example may be made of metal. Optionally, the percussion massager 100 or temperature-controlled massage node 102 may further or alternatively include a fan for active cooling. Further, the housing 402 may be designed to operate as the heat dissipating or absorption device 404 or may assist the heat dissipating or absorption device 404, for example, by incorporating venting in the housing. For example, perforations, may be incorporated into the housing 402.

A thermal conductor (not shown), such as a thermal paste, may be positioned between the Peltier plate 406 and the contact medium 408 to transfer heat and/or cold between the Peltier plate 406 and the contact medium 408. The Peltier plate 406 may be, for example, a single Peltier chip with reverse polarity for heating and cooling. While the illustrated examples show the use of only one single Peltier plate or chip 406, more than one plate or chip may also be utilized in different configurations, such as by stacking the chips or positioning the chips side-by-side.

While the temperature-controlled massage node 102 of the present invention may be attached or affixed to the piston 212 or, alternatively may be removably coupled to the piston 212, the example illustrated in FIG. 4 illustrates the temperature-controlled massage node 102 attached to the piston 212. Here, the node housing 402 includes a top cylindrical recessed portion 405 for receiving the bottom end of the piston 212. The piston 212 includes two spaced apart annular rings 407 surrounding the piston 212 near its center creating a groove between the annular rings 407. The groove created by the rings 407 receives a corresponding circular tongue 409 on the flexible cap 308 to retain the flexible cap 308 against the piston 212.

At least one electrical connector or contact 410 is also positioned directly under the cylindrical recessed portion 405 of the node housing 402 in the center of heat sink 404 and in communication with the Peltier plate 406 to provide power to the Peltier plate 406. Openings in the top of the cylindrical recessed portion 405 of the node housing 402 allow for flexible wires (not shown) to contact the electrical contacts 410 to power the Peltier plate 406. Flexible wires draw electricity from the power source 200 in the massager housing 104 and extend from the circuit board 205 through the center of the piston 212 to contact the electrical connectors 410. The flexible wires must maintain enough slack when attached to the electrical connectors 410 to prevent the contacts from detaching from the connectors 410 during use and/or while the temperature-controlled massage node 102 percusses. Further positioned around the top of the piston 212 above the flexible cap 308 is a slidable sleeve 412, a middle sleeve 414 and an outer sleeve 416 which engage the mounting brackets 420 positioned on the interior of the forward housing 108.

Alternatively, similar to when the temperature-controlled massage node 102 is removably coupled to the piston 212 (as will be explained further below), the piston 212 may include electrical contact pins, plates, leaf spring plates, rings or pin receptacles and the temperature-controlled massage node 102 may include a corresponding electrical contact pins, plate, leaf spring plate, or ring to close the circuit in communication with the Peltier plate 406 for mating with the electrical contacts of the piston 212 when the temperature-controlled massage node 102 is coupled to the piston 212 to provide power to the Peltier plate 406.

Figure 5A:
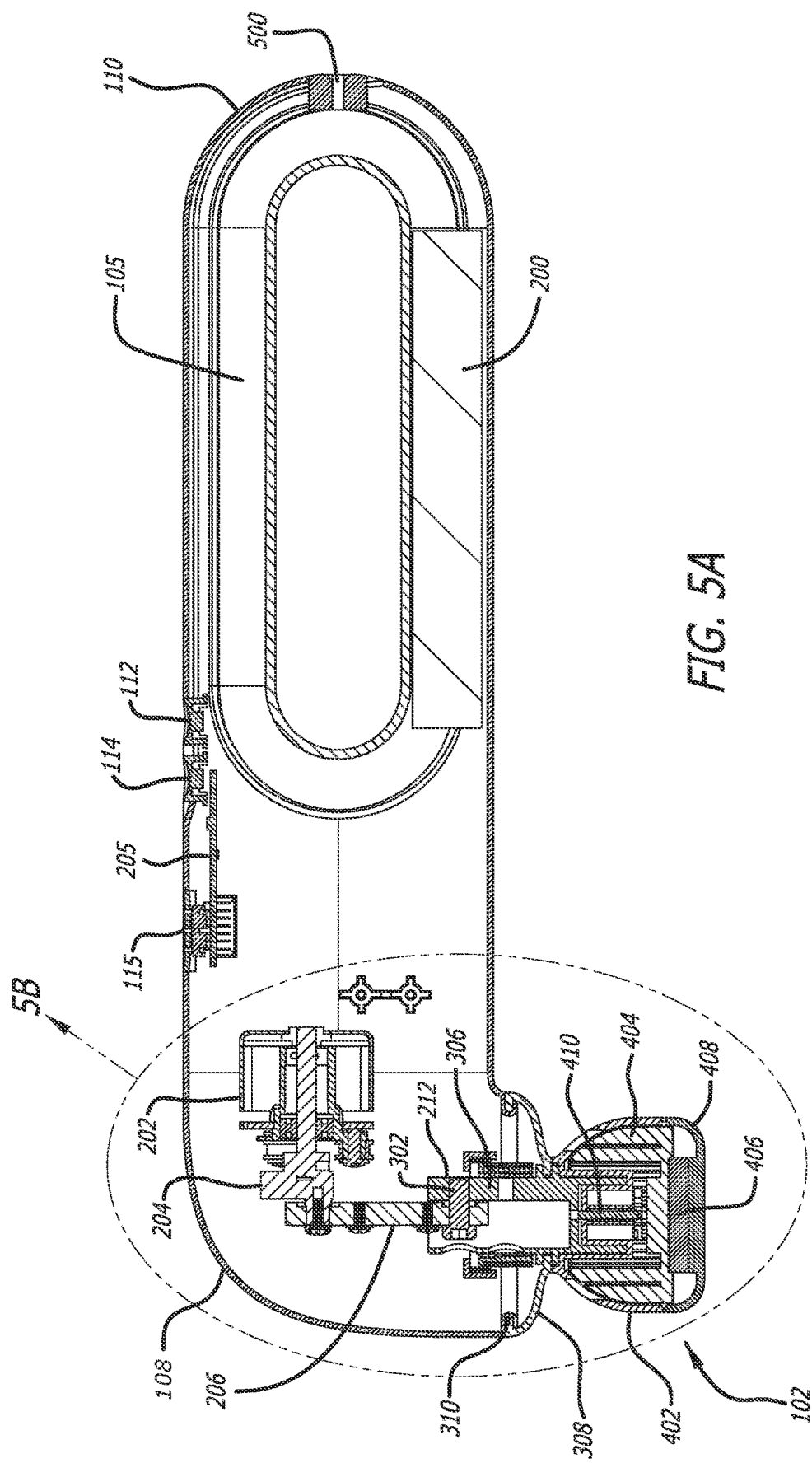
FIG. 5A illustrates a cross-section of the portable handheld percussion massager of FIG. 1 taken along line 5A-5A of FIG. 1.
Figure 5B:
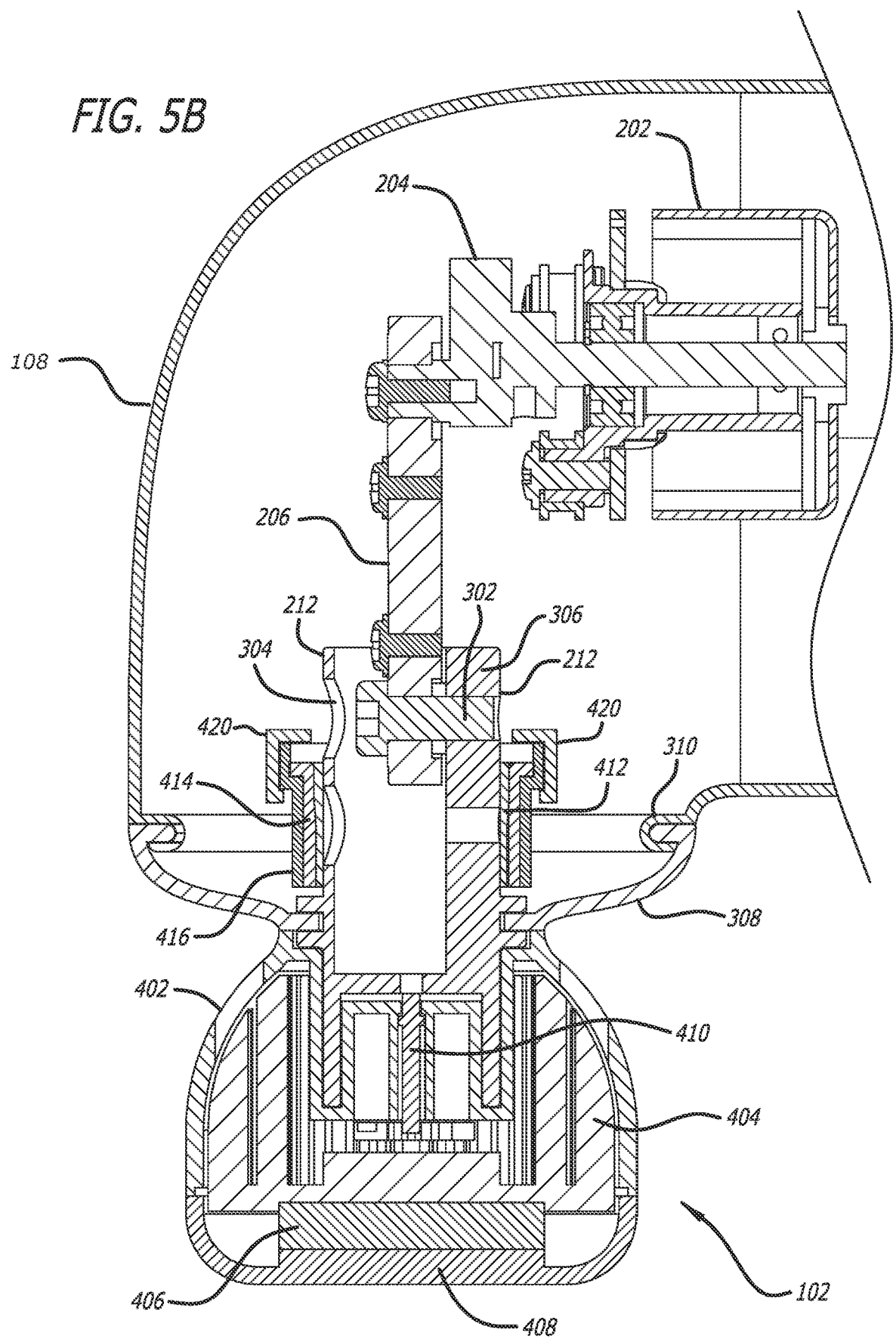
FIG. 5B is an enlarged view of the encircled portion 5B of the portable handheld percussion massager of FIG. 5A.

FIG. 5A illustrates a cross-section of the portable handheld percussion massager 100 of FIG. 1 taken along line 5A-5A of FIG. 1. FIG. 5B is an enlarged view of the encircled portion 5B of the handheld percussion massager of FIG. 5A. FIGS. 5A and 5B together illustrate the attachment of the temperature-controlled massage node 102 to the piston 212 and forward housing 108.

As illustrated in FIGS. 5A and 5B, motor 202 rotatably drives the crankshaft 204 which is coupled to the rod 206, where the rod 206 is attached to the crankshaft 204 offset from the rotational axis of the crankshaft 204. Rod 206 is then attached to the piston 212 at its end opposing the crankshaft 204, and the piston 212 is attached to the massage node 102. Massage node 102 includes a node housing 402 which receives the end of the piston 212 opposing its attachment to the rod 206. Electrical contacts or connections 410 are exposed through top of the node housing 402 under the piston 212 to make electrical connections or contact with flexible wires extending from the circuit board 205 through the hollow center of the piston 212. Electrical contacts 410 provide power to the Peltier plate 406 which is positioned under the heat sink 404. Heat sink 404 is positioned under and around the piston 212 within the node housing 402. A contact medium 408 is also provided over the Peltier plate 406 to prevent direct contact by a user with the Peltier plate 406. Also shown on FIG. 5A is an electrical connector 500 for recharging the battery 200.

Figure 6:
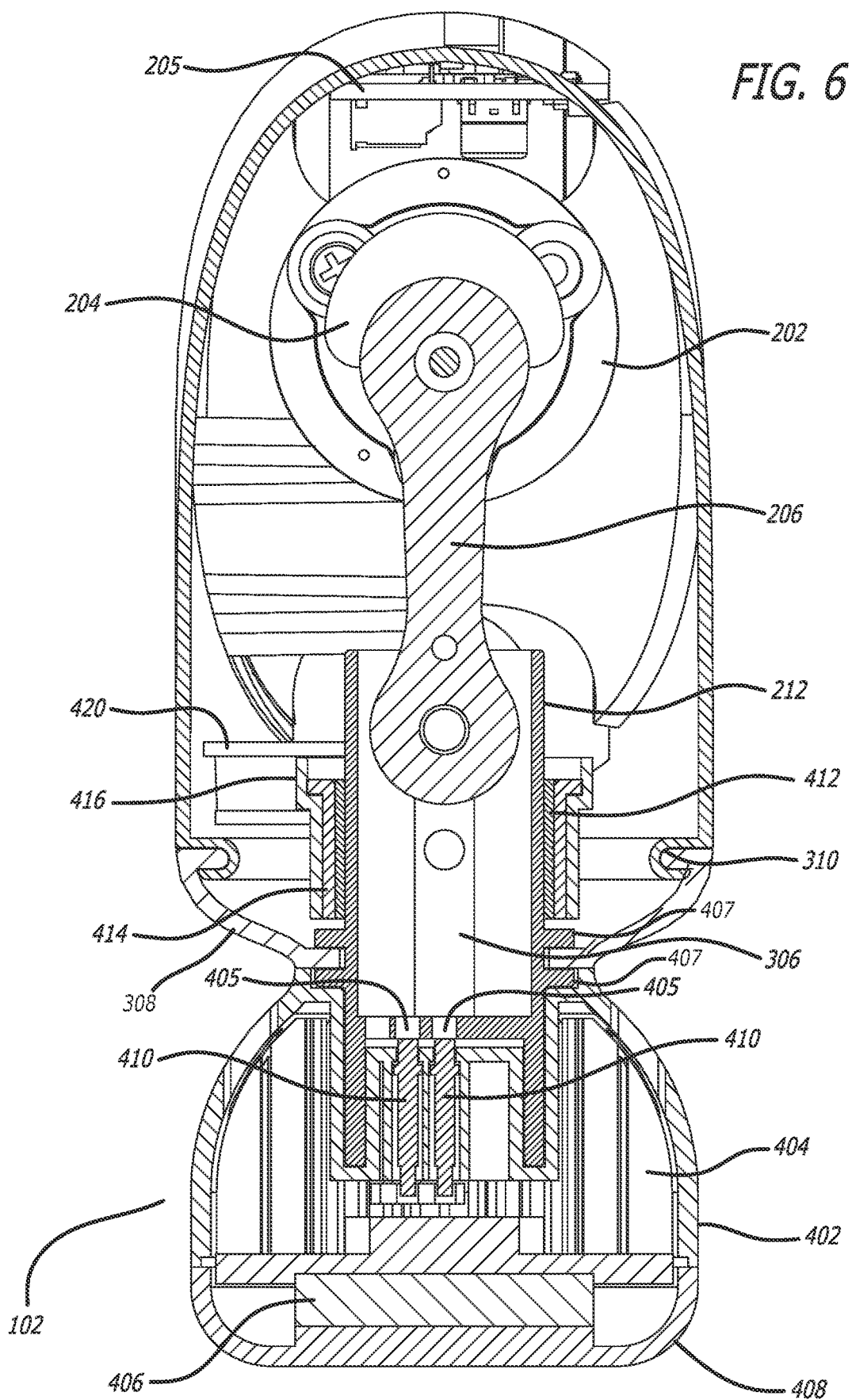
FIG. 6 illustrates a cross-section of the portable handheld percussion massager of FIG. 1 taken along line 6-6 of FIG. 1.

FIG. 6 illustrates a cross-section of the handheld percussion massager 100 of FIG. 1 taken along line 6-6 of FIG. 1. FIG. 6 illustrates the connection of the rod 206 to the piston 212 along the hollow upper portion of the piston 212. Electrical contacts 410 are best seen in FIG. 6, which also illustrates the exposure of the electrical contacts 410 to the hollow cylindrical opening in the piston 212. The Peltier plate 406 is positioned between the heatsink 404 and the contact medium 408 in communication with the electrical contacts 410. The two rings 407 on the piston 212 having an annular groove between the rings 407 that engage the tongue on the flexible cap 308 is also seen in FIG. 6.

Electrical contacts 410 are positioned in the node housing 402 in the center of heat sink 404 and in communication with the Peltier plate 406 to provide a power to the Peltier plate 406. Openings in the top of the cylindrical recessed portion 405 of the node housing 402 align with openings in center of the piston 212 to allow for flexible wires (not shown) to contact the electrical contacts 410 to power the Peltier plate 406. The slidable sleeve 412, middle sleeve 414 and outer sleeve 416 which engage the mounting brackets 420 positioned on the interior of the forward housing 108 around the top of the piston 212 above the flexible cap 308 is also best seen in FIG. 6.

Figure 7:
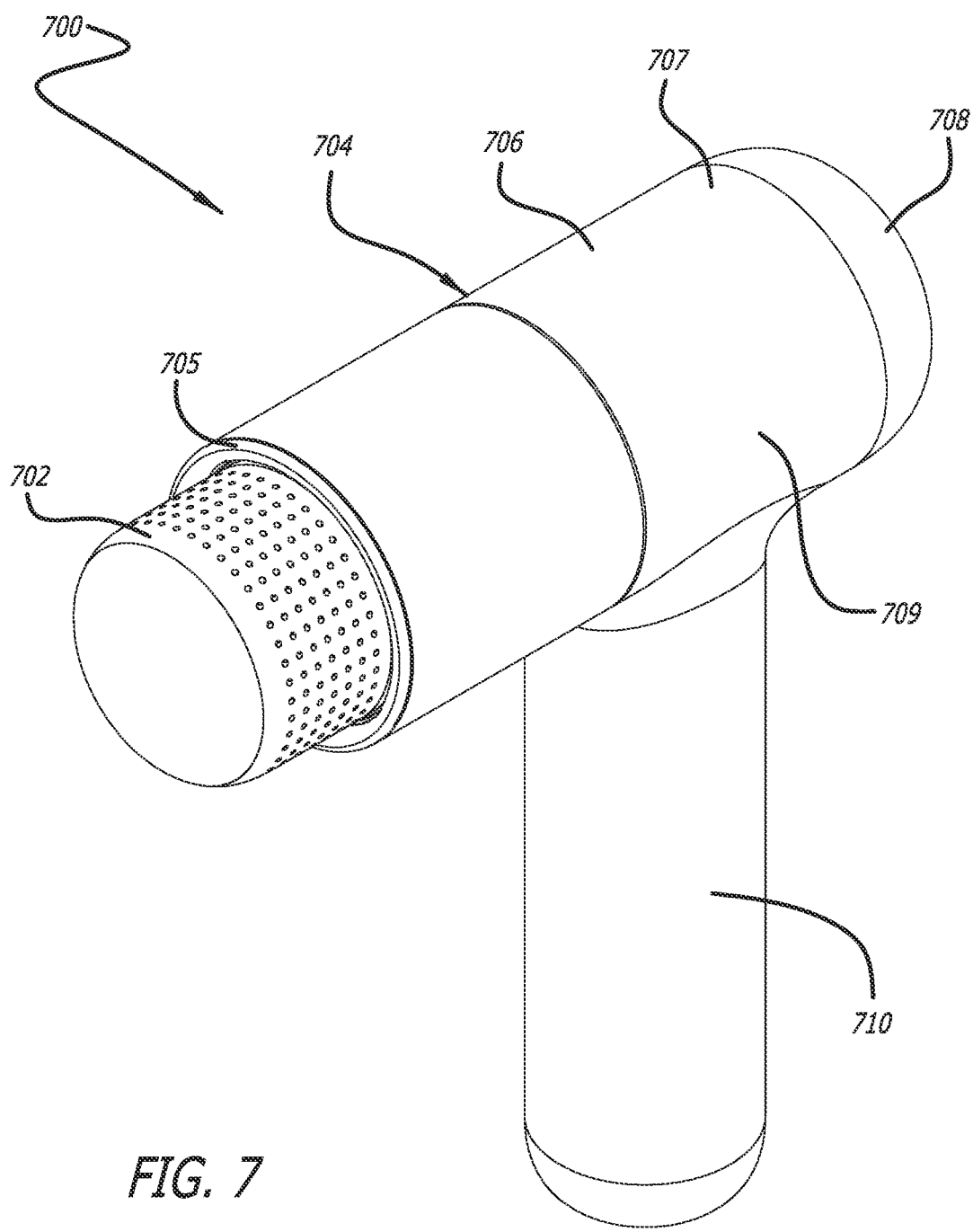
FIG. 7 illustrates a side perspective view of another example implementation of a portable handheld percussion massager of the present invention.
Figure 8:
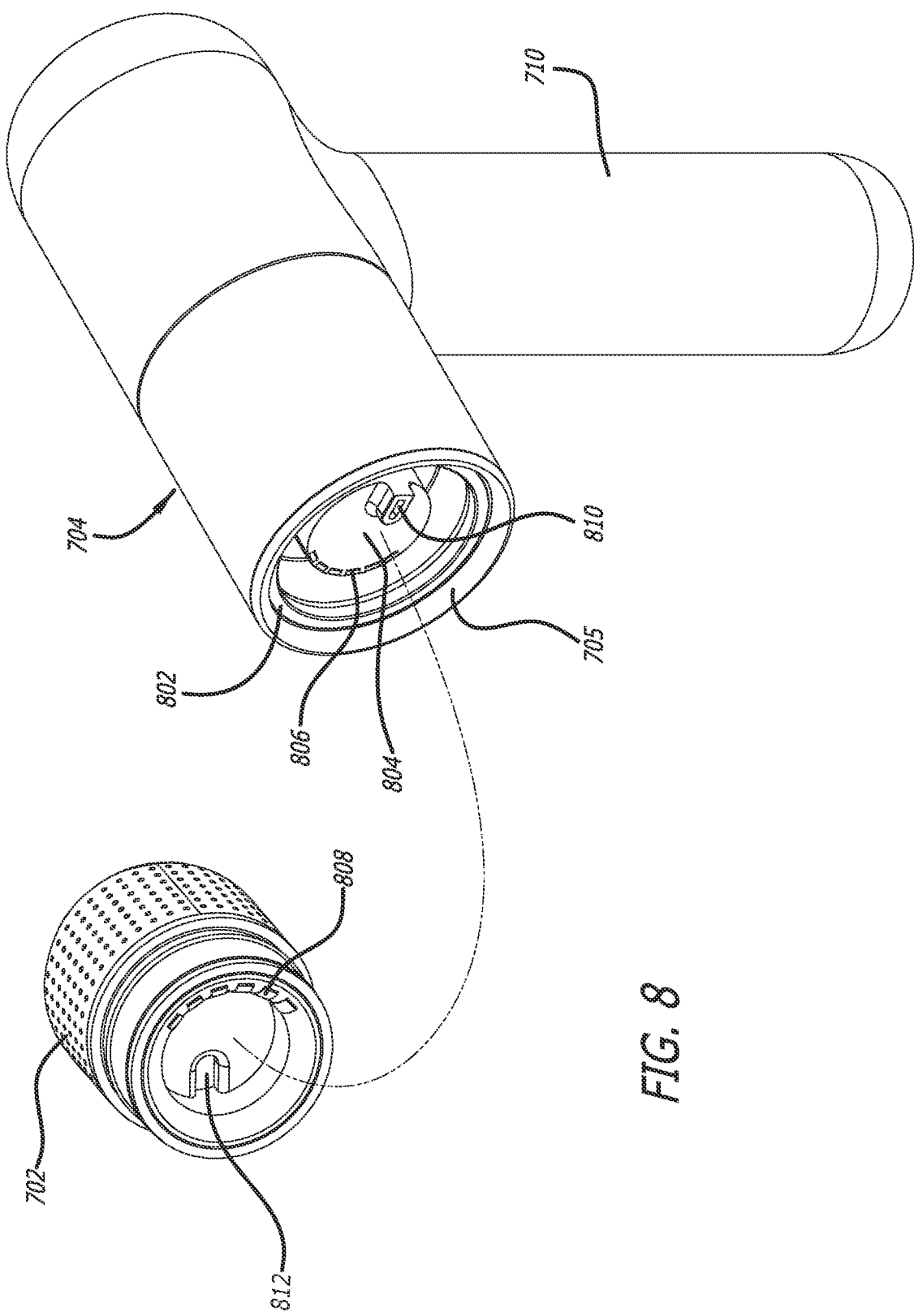
FIG. 8 illustrates a side perspective view of the portable handheld percussion massager of FIG. 7 with the massage node removed.
Figure 9:
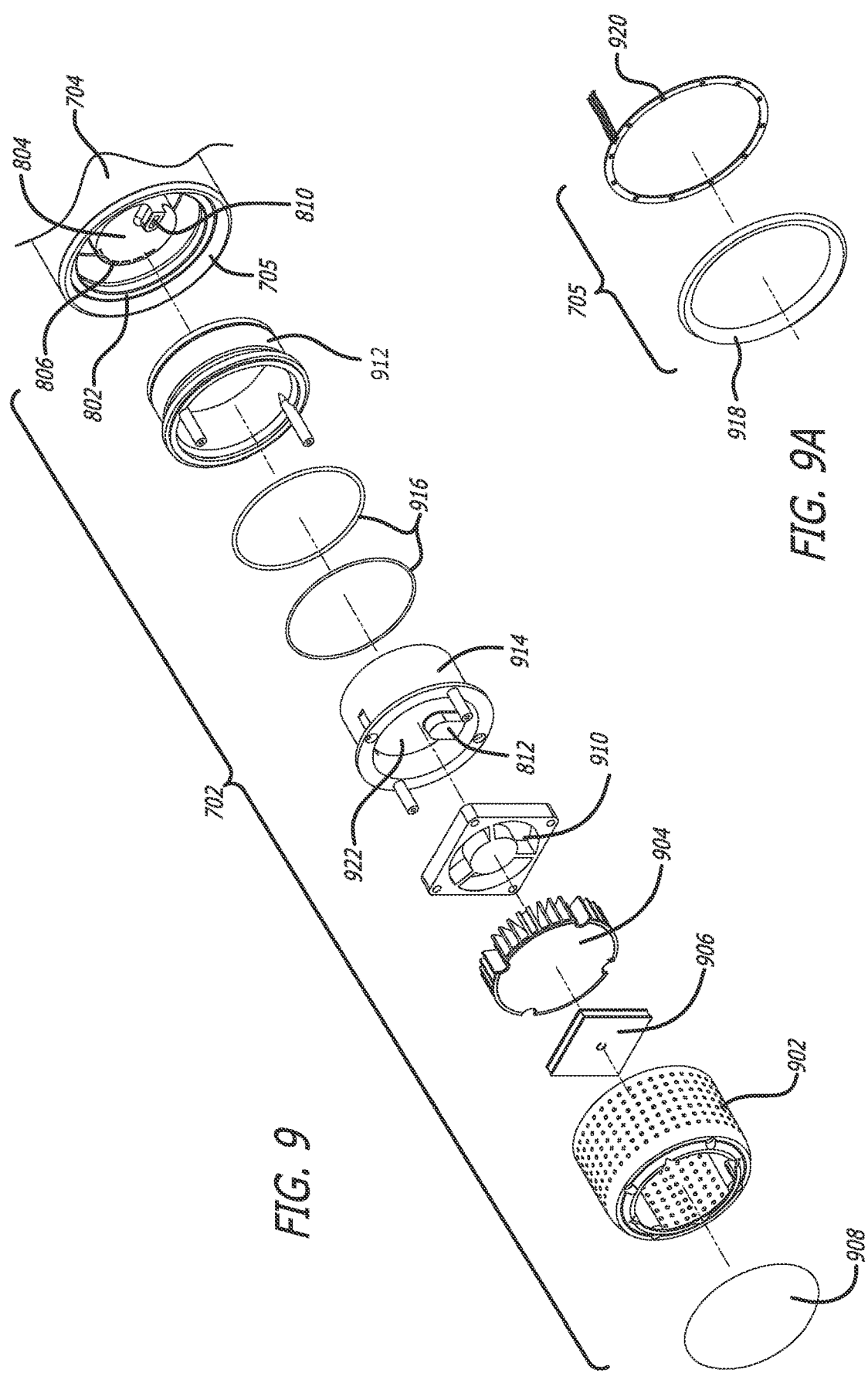
FIG. 9 illustrates an exploded view of the massage node of FIG. 8.

FIG. 7-15 illustrate yet another example of an implementation of the present invention. In FIG. 7-1.5, temperature-controlled massage node 702 is illustrated that can be removable coupled to a portable handheld percussion massager 700. In this example, a light ring 705 is also positioned on the body of the massager to indicate the state of the temperature-controlled massage node 702. In this example, the light ring 705 is an annular ring coupled or attached to the front end peripheral edge of the massager body or housing 704. While illustrated at attached to the front peripheral edge of the massager body or housing 704, the light ring could be integrated anywhere along the massager body or housing 704. Optionally, the light ring 705 could also be made part of the temperature-controlled massage node 702 itself, for example, by incorporating the light ring 705 into the node housing 902 (FIG. 9).

FIG. 7 is a side perspective view of the portable handheld percussion massager 700. As illustrated in FIG. 7, the portable percussion massager 700 includes a massager housing 704 having a main body 706, rear panel 708 and a handle 710. In this example, the handle 710 may be formed extending downward from the main body 706. The main body 706, rear panel 708 and a handle 710 may be constructed from one or more pieces to form a hollow massager housing 704. For example, the main body 706 and the handle 710 may be constructed from be two separate pieces—a right side piece 707 and a left 709 side piece that engage one another to form a hollow massager housing 704, The rear panel 708 may also be a separate piece engaged to the rear of the main body 706. These examples are not limiting. The massager housing 704 may be made from any number of different pieces formed together or separately.

Figure 10:
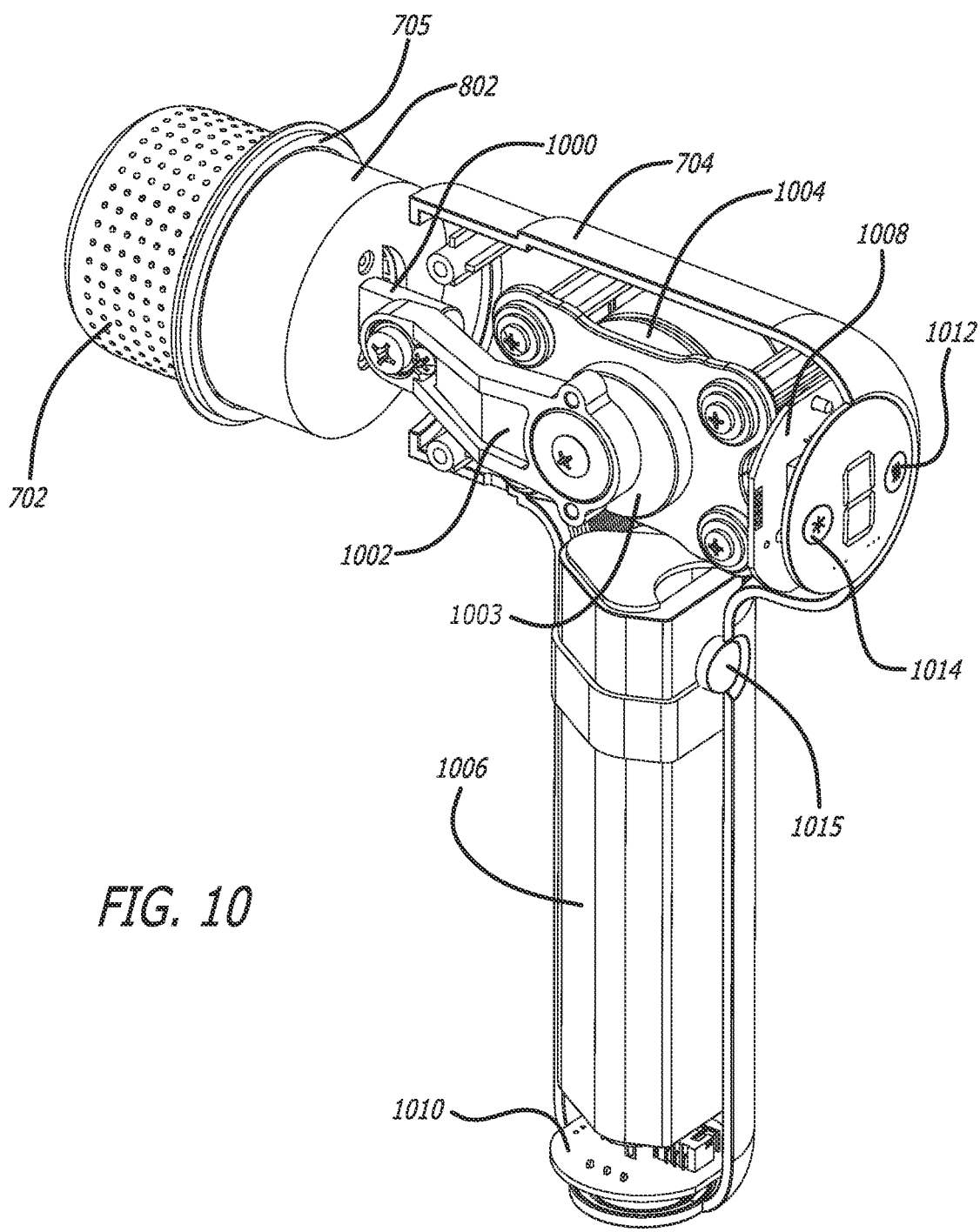
FIG. 10 illustrates a side perspective view of the portable handheld percussion massager of FIG. 7 with the side panel of the massager housing removed.

FIG. 8 illustrates a side perspective view of the portable handheld percussion massager 700 of FIG. 7 with the massage node 702 removed. As shown, the massage node 702 is removably coupled to a node mount 802 that is driven by the massage piston 1000 (FIG. 10). Here, the massage node 702 is attached to a node mount 802 though a friction fit or press fit, that creates an interference or transition type fit; however, other known mechanisms for coupling the massage node 702 to the node mount 802 may be provided, including but not limited to, for example, threading. As will be explained further below, and shown in connection with FIG. 9, in the illustrated example, the massage node 702 includes at least one sleeve or shaft having component parts that couple with parts on the interior of the node mount 802 to removably couple, through a press fit, the massage node 702 to the massage housing 704.

In this example, the node mount 802 includes a mating pad 804 having at least one electrical contact pin, plate or leaf spring plate 806 for making contact with at least one corresponding electrical contact pin, plate or leaf spring plate 808 on the massage node 702. The corresponding electrical contact pin, plate or leaf spring plate 808 on the massage node 702 are in communication with a thermoelectric heating and cooling device 914 (FIG. 9) when the temperature-controlled massage node 702 is coupled to the node mount 802. The node mount 802 further includes a male connector 810 on the mating pad 804 that corresponds to a female connector 812 in the massage node 702 for aligning the massage node 702 when inserted into the massager housing 704 such that the electrical contact pins and/or plates 806 and 808 align to make electrical contact. As set forth above, the electrical contacts 808 and 806 may be electrical contact pins, plates, leaf spring plates or rings. Optionally, contactless charging may also be used.

FIG. 9 illustrates an explode view of the massage node 702 of FIG. 8. In this example, temperature-controlled massage node 702 includes a node housing 902, a heat dissipating or absorption device 904, and at least one thermoelectric heater/cooler 906, often referred to as a Peltier plate or chip, and a contact medium 908 for covering the Peltier plate 906 to help dissipate the heating and cooling effect of the Peltier plate 906 and transfer the heating or cooling effect to the user. The heat dissipating or absorption device 904 may be, as illustrated, a heat sink, which in this example may be made of metal. The contact medium 908 may be, for example, be an aluminum or stainless steel plate (or other thermal conductive metal) and may be formed as part of the node housing 902 or be a separate piece from the node housing 902. As with the prior example in FIGS. 1-6, a softer material may be used in connection with the thermal conductive plate or in place of the thermal conductive plate, such as a thermal conductive cloth like pad or material, which may be made, for example, from cloth, plastic, graphite, carbon fiber and/or a silicon material (such as a gel or resin) having conductive fibers, to name a few examples.

Optionally, the percussion massager 700 or temperature-controlled massage node 702 may further or alternatively include a fan 910 for active cooling. In this illustration, the fan 910 is positioned underneath the heat sink 904 is in communication with the electrical contact pins and/or plates 808 to power the fan 910 when the node 702 is coupled to the massager housing 704. To couple the massage node 702 to the housing, the massage node 702 includes at least one mounting sleeve or shaft for coupling the massage node 702 to the massager body or housing 704, which in this example, includes an outer sleeve 912 and inner sleeve 914 and sealing rings 916 positioned therebetween. The outer sleeve 912 includes grooves for interlocking with corresponding grooves on the interior of the massage node mount 802 for creating a friction fit between the massage node 702 and massager housing 704, when the massage node 702 is inserted in the massage node mount 802 of the massager housing 704.

The inner sleeve 914 includes a recessed plate 922 for receiving the mating pad 804. The recessed plate 922 includes the female connector 812 for receiving the male connector 810 of the mating pad 804 and electrical contact pins or plates 808 for contacting and aligning with the electrical contact pins or plates 806 on the mating pad 804.

Also, shown in FIG. 9A is light ring 705 as it would appear removed from the massager housing 704. The light ring 705 functions as an indicator display and includes a transparent or translucent light ring cap 918 and a circular light emitting diode (LED) ring mount 920, having at least one or a plurality of LEDs positioned about the LED ring mount 920 on the surface of the mount (i.e., mount surface). The light ring mount 902 is then electrically connected to the printed circuit board (PCB) or controller 1008 (FIG. 10) to control the operation of the LED(s). The LED(s) may include single, dual or multicolor LEDs, connected in series or parallel, that can be activated to illuminate together or separately to display different colors, resulting in the illumination of one or more same color LED or one or more LEDs of differing colors to produce different visible illuminating effects. The one or more LEDs position on the ring mount can be electrically connected to one or more of the LEDs on the ring mount or directly to the PCB 1008. The at least one LED or plurality of LEDs are controlled by the PCB 1008 for illumination upon the occurrence of certain operations of the massager 700 or the massage node 702.

While the light ring 705 is illustrated attached or coupled to the massager body 704, it could alternatively be included as part of the massage node 702, by integrating the light ring 705 with, or attached above or below, the node housing 902. In this manner, power can be supplied to the light ring 705 by a power source in the massage node 702. Power may also be supplied to the light ring 705 on the massage node 702 by a power source in the massage body 704 to illuminate the LEDs in the light ring 705 in the same manner as the thermoelectric heating and cooling device 914 (FIG. 9) receives power. For example, if the light ring 705 is integrated into the massage node 702, corresponding electrical contact pin, plate or leaf spring plate 808 on the massage node 702 could be connected to, or in communication with, the light ring 705 to power to the light ring 705. When included with the massage node 702, Again, a thermal conductor (not shown), such as a thermal paste, may be positioned between the Peltier plate 906 and the contact medium 908 to transfer heat and/or cold between the Peltier plate 906 and the contact medium 908. The Peltier plate 906 may be, for example, a single Peltier chip with reverse polarity for heating and cooling. While the illustrated examples show the use of only one single Peltier plate or chip 906, more than one plate or chip may also be utilized in different configurations, such as by stacking the chips or positioning the chips side-by-side.

FIG. 10 illustrates a side perspective view of the portable handheld percussion massager 700 of FIG. 7 with the right-side panel of the massager housing 704 removed. As shown, the portable handheld percussion massager 700 includes a piston 1000, rod 1002 and crankshaft 1003 driven by a motor 1004 via a motor shaft, which imparts a percussion massage effect on the node mount 802 that drives the nodes 702 connected thereto. The piston 1000 is coupled to the node mount 802, that then couples to the massage node 702, as illustrated in FIG. 9. The motor 1004 rotatably drives a crankshaft 1003 which is coupled to the piston 1000 by rod 1002 to create a percussive massage effect by moving the node mount 802 and coupled massage node 702.

As with the example in FIGS. 1-6, a battery 1006 and circuit board/controller 1008 are also provided to control the operation of the massager 700. All the same optional power sources that were discussed in connection with FIGS. 1-6 are applicable to this example massager 700, including the massage node 702 having its own independent power source to control its operation from hot to cold, and or even to provide a vibrating massage effect in addition to, in combination with, or absent any percussive massage effect.

Further, in the illustrated example, controls 1012, 1014 and 1015 may be positioned on the massager housing 704, with, for example, a liquid crystal display, that allows users to monitor and control the operation of the percussion massager 700. For example, the user may turn the percussion massager 700 on and off using user control 1015 or may also use other separate controls (not shown). The user can also use controls 1012 and/or 1014 to control the various speeds of the motor 1004, to create different percussion massage effects and further control the hot and cold effects imparted by the temperature-controlled massage node 702 when the heating and cooling effects are engaged. Additional controls/lighting elements 1010 may also be provided in certain implementations to convey further operational information to the user and/or allow the user to control other operations of the massager 700.

As described above and further explained below, a light ring 705 may also be provided on the massager housing 700 to communicate the state of the operation of the percussion massager 700 and/or the massage node 702 to the user. Here, the light ring 705 may include one, more or a plurality of LEDs, which may be either or both single, dual or multicolor LEDs that may be illuminated, for example, when the massager 700 is on or, in response to, or corresponding with, certain operational conditions. The LEDs may light all together, may illuminate with less than all of the LEDs (for example half at a time) or may illuminate in sequence or on another pre-programmed routine or schedule to create different lighting effects. The LEDs may function alone or in connection with other lights on the massager 700 as indicator lights or an indicator display that may be illuminated to indicate any number of operational conditions. For example, indicator lights may indicate the speed of operation of the motor 1004 of the percussion massager 700. Indicator lights may also be illuminated to indicate whether the temperature-controlled massage mode 702 is operating, whether the temperature-controlled massage nodes 702 are operating in a heating mode or a cooling mode (e.g., red verse blue LED lights), at which preset temperature the temperature-controlled massage node 702 is operating, the state of the battery and/or the speed of the motor, among other things. For example, the LEDs may illuminate different hues of light for different operation, a first hue, second hue, or a shade of red/shade of blue, etc.

Figure 11:
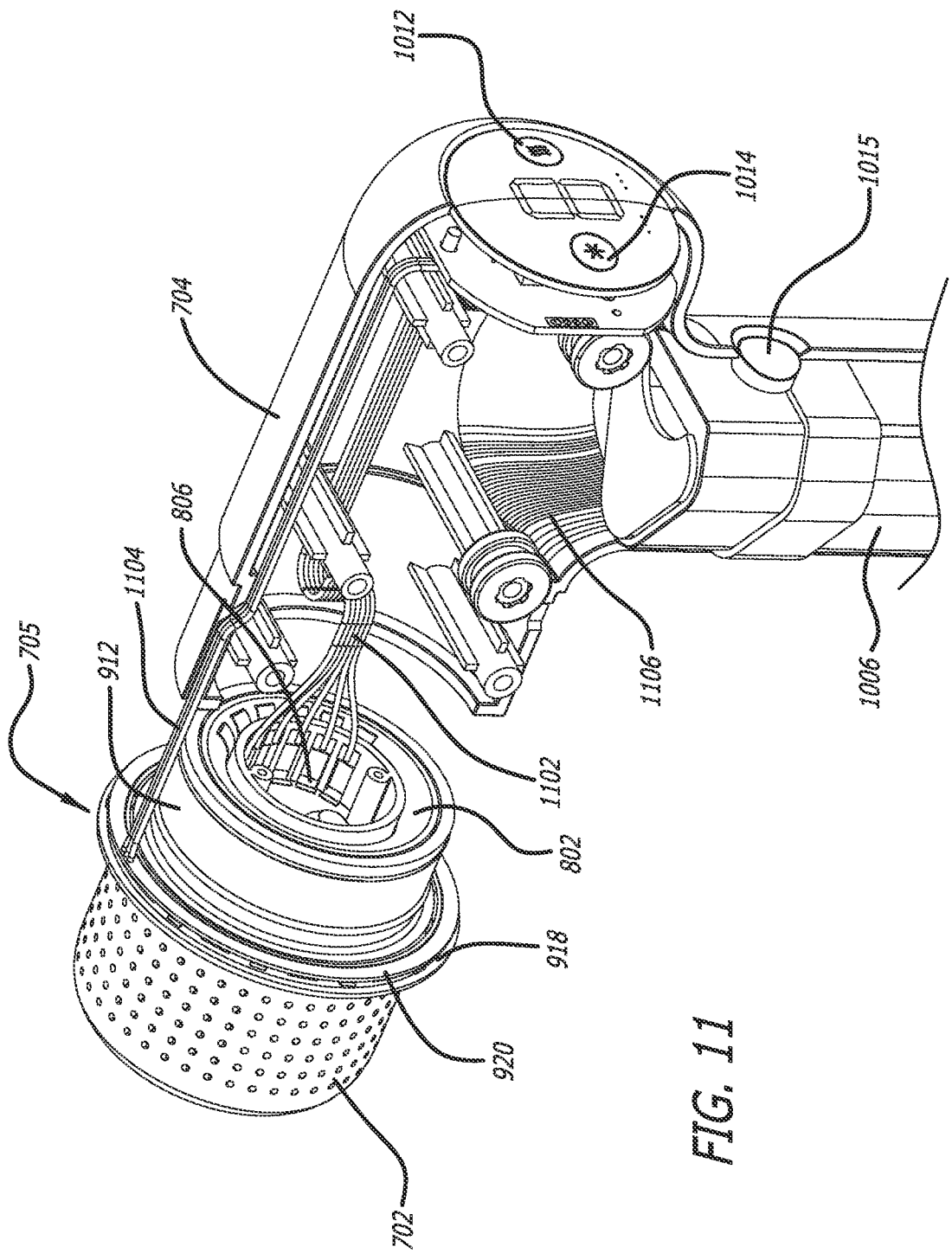
FIG. 11 illustrates a side perspective view of the portable handheld percussion massager of FIG. 10 with the motor, piston and side panel of the massager housing removed.

FIG. 11 illustrates a side perspective view of the portable handheld percussion massager 700 of FIG. 10 with the motor 1004, crankshaft 1003, rod 1002 and left side panel 709 of the massager housing 704 removed to expose the circuitry of the massager 700. As shown, electrical circuitry 1106 runs from the battery 1006 to power the motor 1004 and electrical circuitry 1202 (FIG. 12) from the battery 1006 to the PCB/controller 1008. Electrical circuitry 1102 also runs from the circuit board 1008 to the electrical contact plates 806 on the mating pad 804. Electrical circuitry 1104 further runs from the circuit board 1008 to the LED light ring 920 to control and power the LEDs on the light ring 920.

Figure 18:
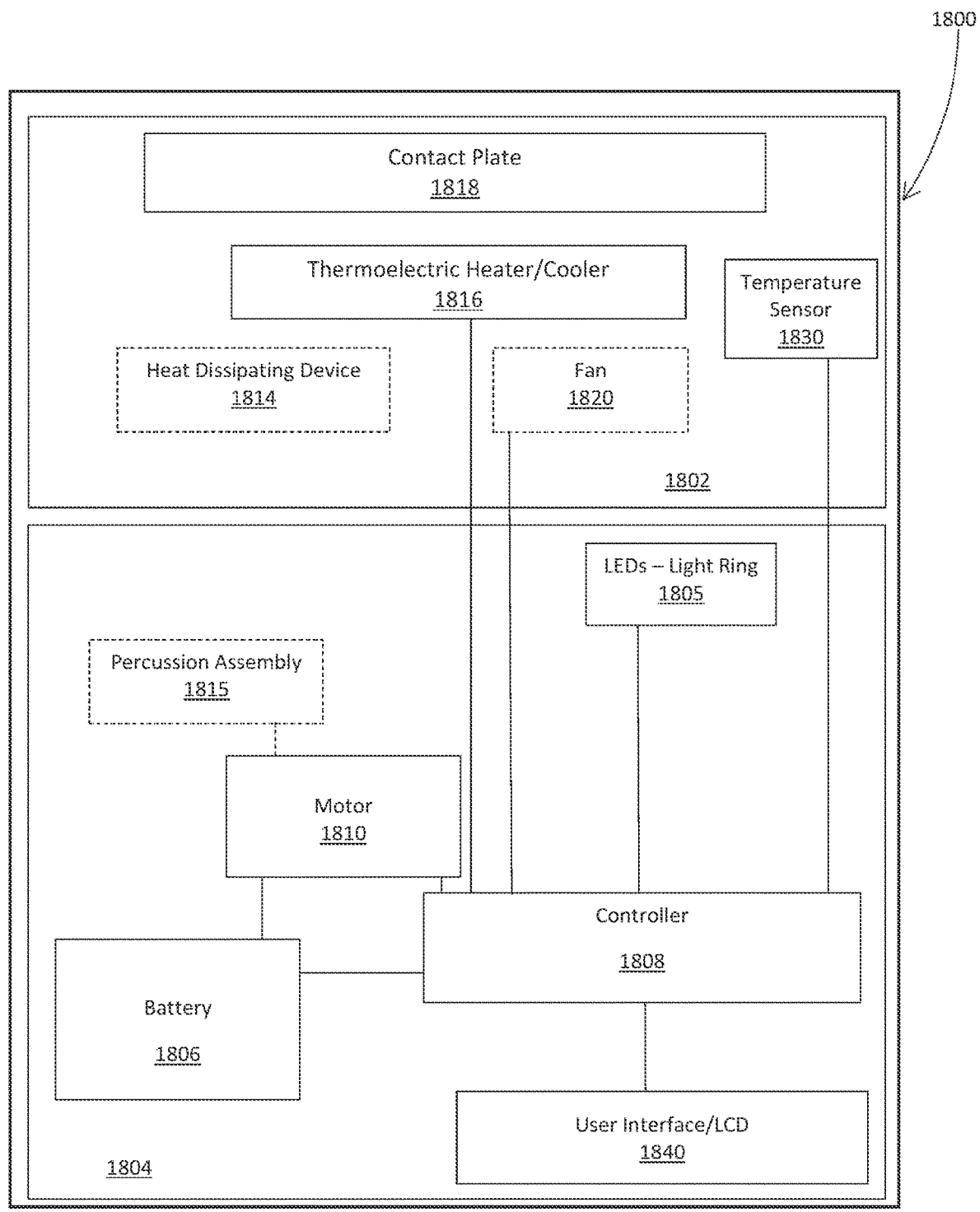
FIG. 18 is a block diagram of one example of an implementation of a portable handheld percussion massager of the present invention having the node affixed to the massager body.
Figure 19:
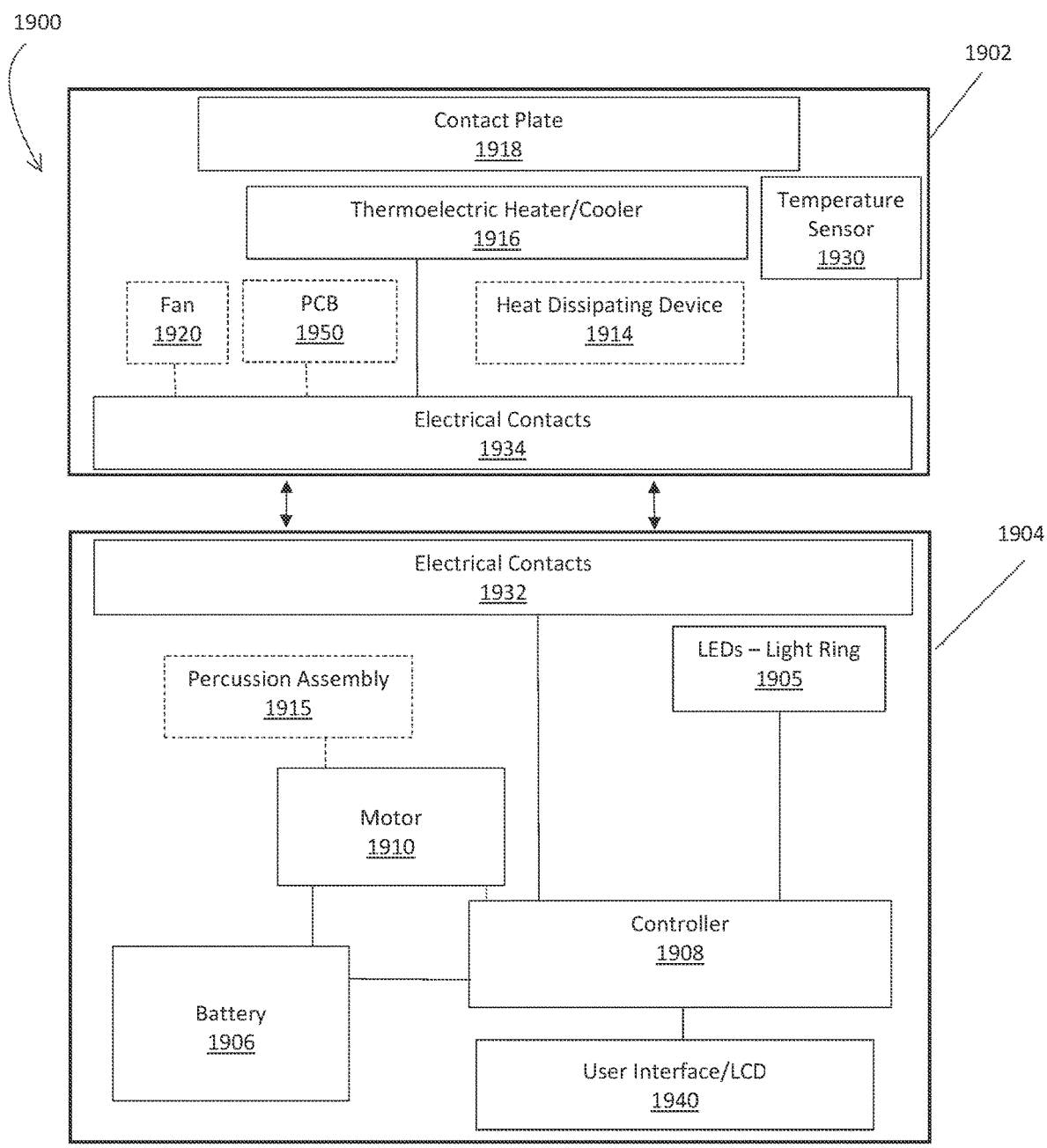
FIG. 19 is a block diagram of one example of an implementation of a portable handheld percussion massager of the present invention having the node removably coupled to the massager body.
Figure 20:
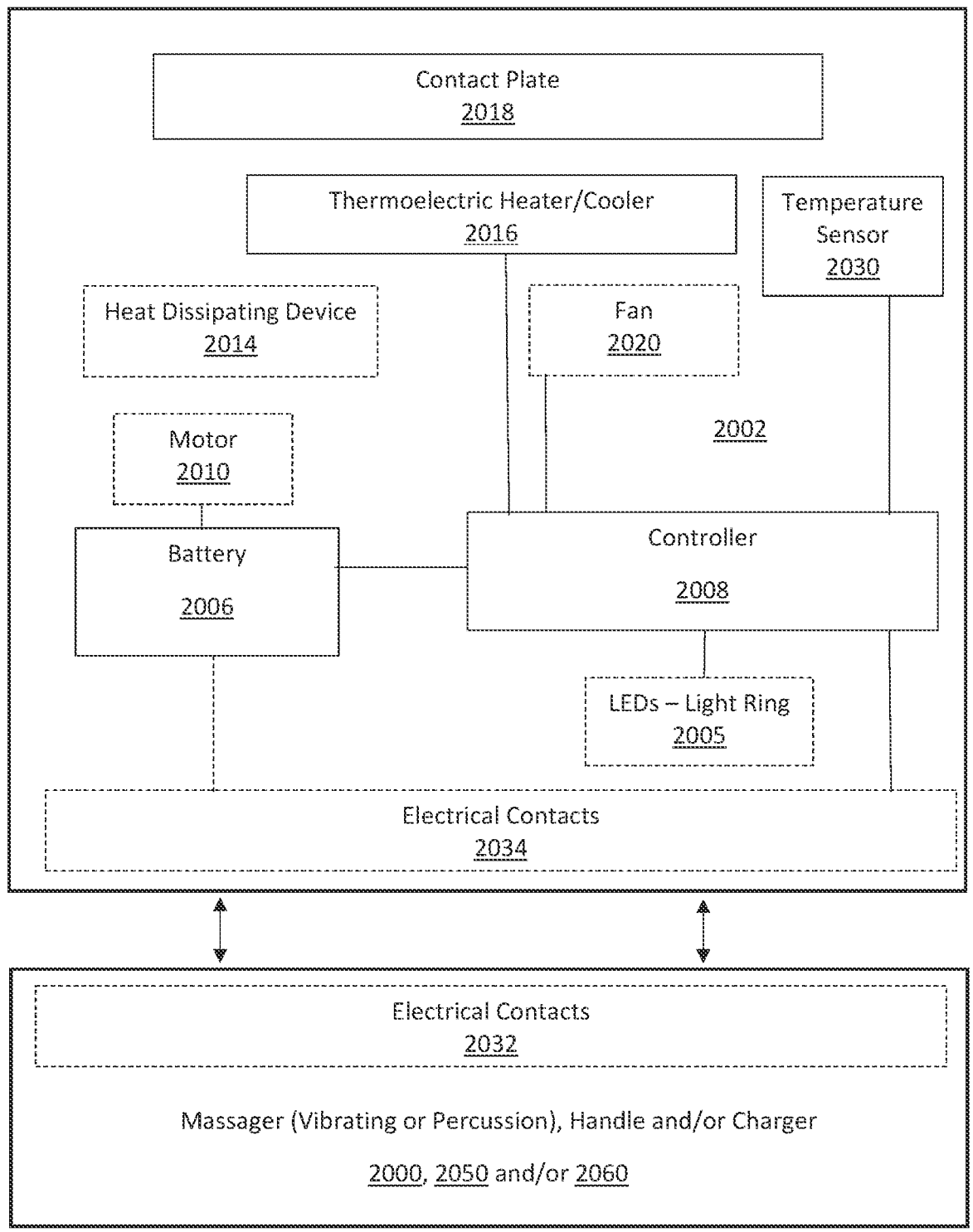
FIG. 20 is a block diagram of one example of an implementation of a portable handheld percussion massager of the present invention having an intelligent massage node.

While any number of contact pins or plates 806 may be used, depending upon the application and component parts in the massage node 702, in the illustrated example, six contact plates 806 are utilized, which includes two pins for the Peltier Plate signal, two pins for the fan signal, and two for a temperature sensor, such as a thermocouple or thermistor (see FIGS. 18-20). Alternatively, three contact pins or plates 806 could also be utilized: a first plate for supplying power, a second plate for ground and a third plate for an IC signal, where a separate PCB and IC in the massage node 702 can parse the signal from the third plate.

Figure 12:
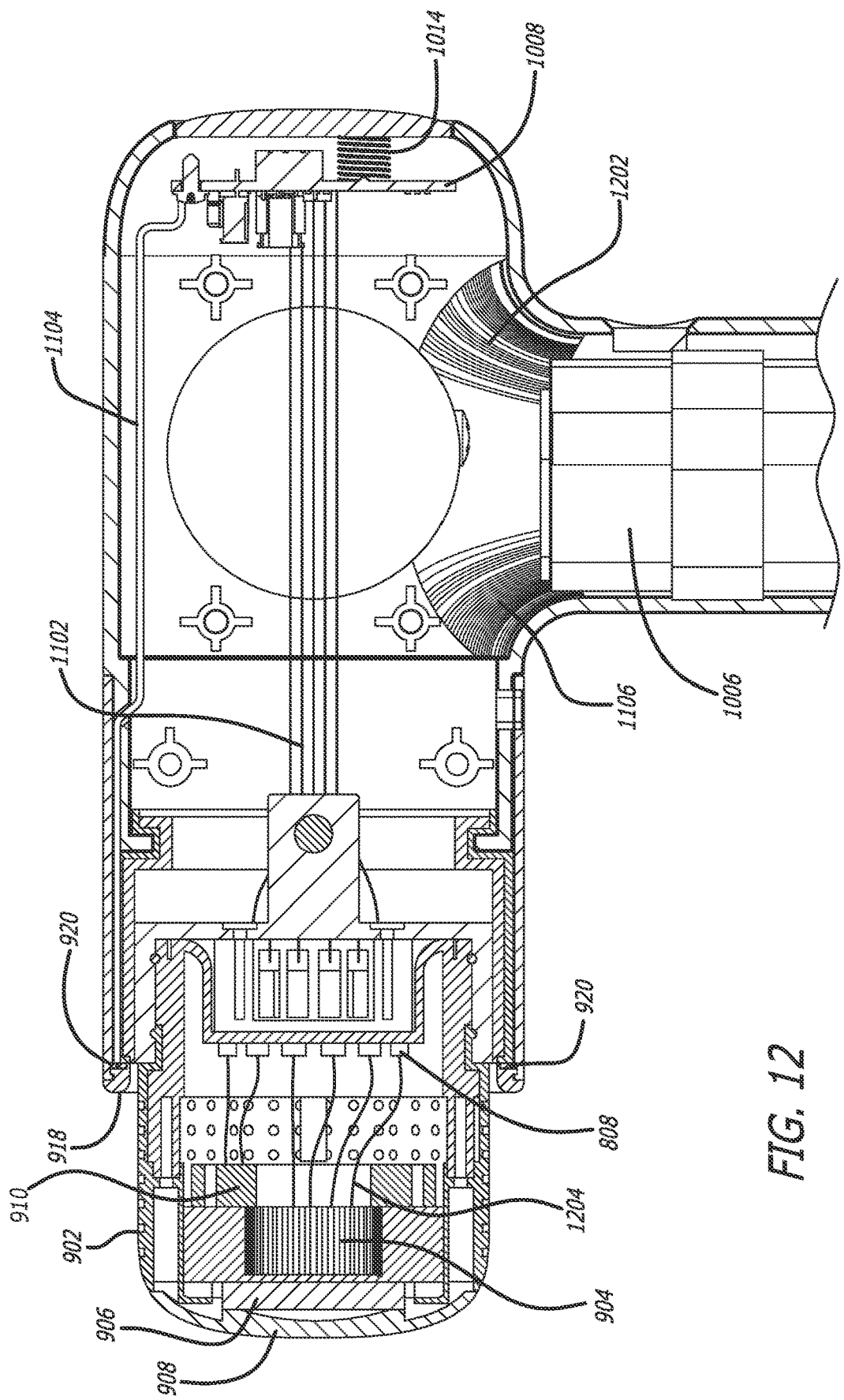
FIG. 12 illustrates a cross-section of the portable handheld percussion massager of FIG. 7.

FIG. 12 illustrates a cross-section of the portable handheld percussion massager 700 of FIG. 7, which illustrates a cross-section of the massage node 702 coupled to the massager housing 704. When coupled to the massager housing 704, the contact pins or plates 806 and 808 form an electrical connection. Again, while any number of contact pins or plates 808 may be used depending upon the application and component parts in the massage node 702, in the illustrated example, six contact plates 808 are utilized. Electrical circuits are then formed by wires 1204 connecting two of the plates 808 to the Peltier Plate 906, two of the plates 808 to the fan 910, and two of the plates 808 to a temperature sensor, such as a thermocouple or thermistor (see FIGS. 18-20). Again, as an alternative, three contact pins or plates 808 could also be utilized: a first plate to provide power, a second plate for ground and a third plate for an IC signal. By establishing this electrical connection, power is provided from the battery 1006 through the controller 1008 to the massage node 702 to control and power the Peltier plate 906, fan 910 and temperature sensor (FIGS. 18-20).

As discussed above, the massager 700 or the massage node 702 may include a light ring 105, comprised of a transparent or translucent light ring cap 918 and a circular light emitting diode (LED) ring mount 920, having at least one or a plurality of LEDs positioned about the LED ring mount 920. The light ring mount 920 is electrically connected to the printed circuit board (PCB) or controller 1008 (FIG. 10) to control the operation of the LEDs. The LEDs are then powered through the controller 1008 by battery 1006.

Figure 13:
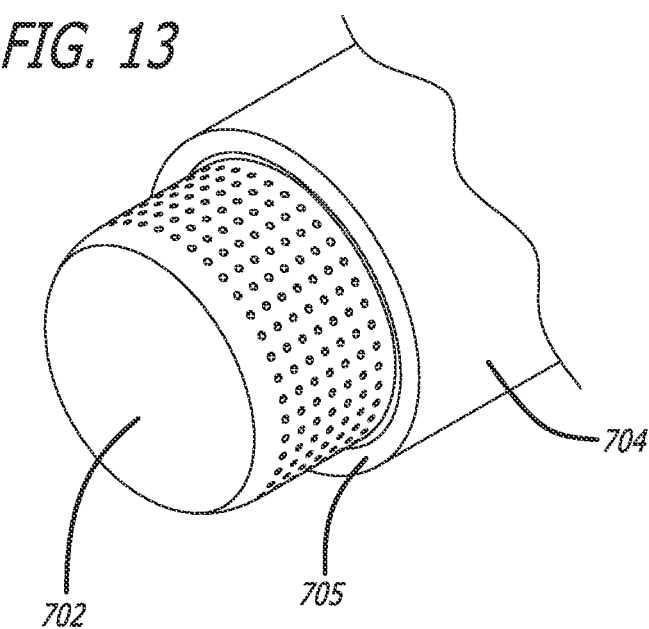
FIG. 13 illustrates a cut away view of the massage node of FIG. 7 showing the light ring turned off.
Figure 14:
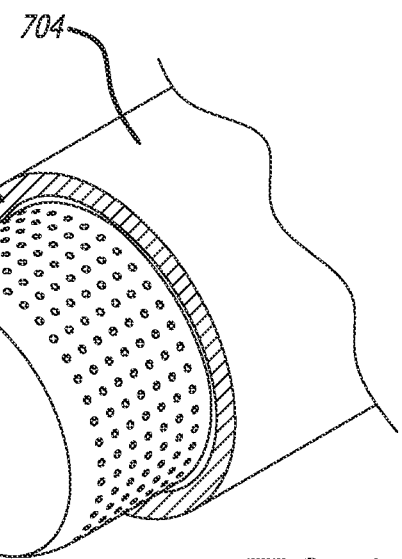
FIG. 14 illustrates a cut away view of the massage node of FIG. 7 showing the light ring operating in a first state or illuminating a first color.
Figure 15:
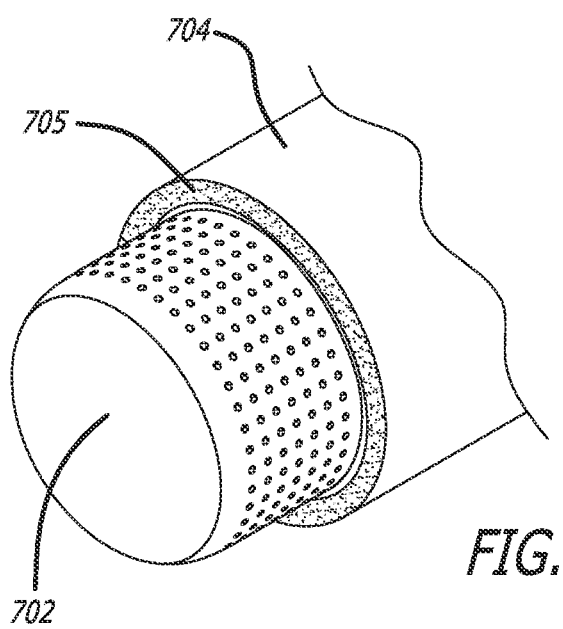
FIG. 15 illustrates a cut away view of the massage node of FIG. 7 showing the light ring operating in a second state or illuminating a second color.

The LEDs can include single, dual or multicolor LEDs and can be activated to illuminate together or separately to display different color lights, illuminate the LEDs in a pattern, illuminate the LEDs sequentially, cause the LEDs to flash or blink and even vary the intensity of the illumination of the LEDs—all to provide many different visual illumination effects. FIGS. 13-15 illustrate, as an example, three different illumination states of the light ring 705, each providing a different illumination effect. Each differing illumination effect indicates a different state of operation of the massager 700 or the massage node 702. For purposes of this application, if the light is a solid color, this will be referred to as a "solid state" of illumination. If the LEDs illuminate in a pattern, illuminate sequentially, flash, blink or vary the intensity of the illumination of the LEDs from the prior illumination states, this state of illumination will be referred to as a "varying state."

FIGS. 13-15 illustrated different states for the light ring 705, each state illuminating differently, corresponding to a state of operation of either or both the massager 700 or massage node 702. FIG. 13 illustrates a cut away view of massage node 702 showing the light ring in a first state. FIG. 14 illustrates a cut away view of massage node 702 showing the light ring in a second state. FIG. 15 illustrates a cut away view of massage node 702 showing the light ring in a third state. While only three states are illustrated, it is recognized the LEDs can illuminate in many more states than represented by FIGS. 13-15 and the present invention is not limited to only the three illuminated states or the examples of corresponding operation providing below.

As set forth above, differing states of operation may be represented with different illuminated colored LEDs or differing LED lighting patterns, intensities, and variations. Of most benefit when used with the temperature-controlled massage node 702 may be the light ring providing different illumination states to show whether the temperature-controlled massage node 702 is operating with or without a heating and/or cooling effect. For example, the first state could represent a ready state or an off state, which represents that the massage node 702 has no heating or cooling effect activated. This illumination state could display without regard to whether the percussive massage effect is being imparted on the massage node 702. Optionally, the illumination state could illuminate, for example, as solid-state white color as a ready state for both the percussion massage effect and the heating and cooling effects when neither is engaged. When the percussion massage effect is illuminated without heating and cooling effects, the solid-state white light could change to a varying state white color to represent that percussive massage effect is engaged, but still without any heating or cooling effect.

The second state may indicate, for example, that the massage node 702 is operating in a cold state, for example, by illuminating in a solid blue. If operated with a percussive massage effect, the LEDs could change to a varying state blue color. Similarly, the third state may indicate, for example, that the massage node 702 is operating in a hot state, for example, by illuminating in a solid red. If operated with a percussive massage effect, the LEDs could change to a varying state red color.

Many different variations can be imaged to illuminate the light ring 705 and are not limited to any examples provided herein. The reference to a first, second, third state or n+1 dates, or a first, second, third or n+1 colors are interchangeable and not limited to the examples provided above. In another example, no illuminate can indicate an off state. A white colored lighted LED ring can indicate a ready state. A red colored LED ring can indicate that the massage node 702 is heated. A blue colored LED ring can indicate that the massage node 702 is cooled. The use of a varied or solid state can be based entirely on design. A varied state could indicate the node is heating up or cooling down, where the illumination becomes a solid-state illumination when the massage node reaches the desired temperature. In this example, the light ring's 705 illumination has no bearing on whether the percussive massage effect is activated.

Figure 16:
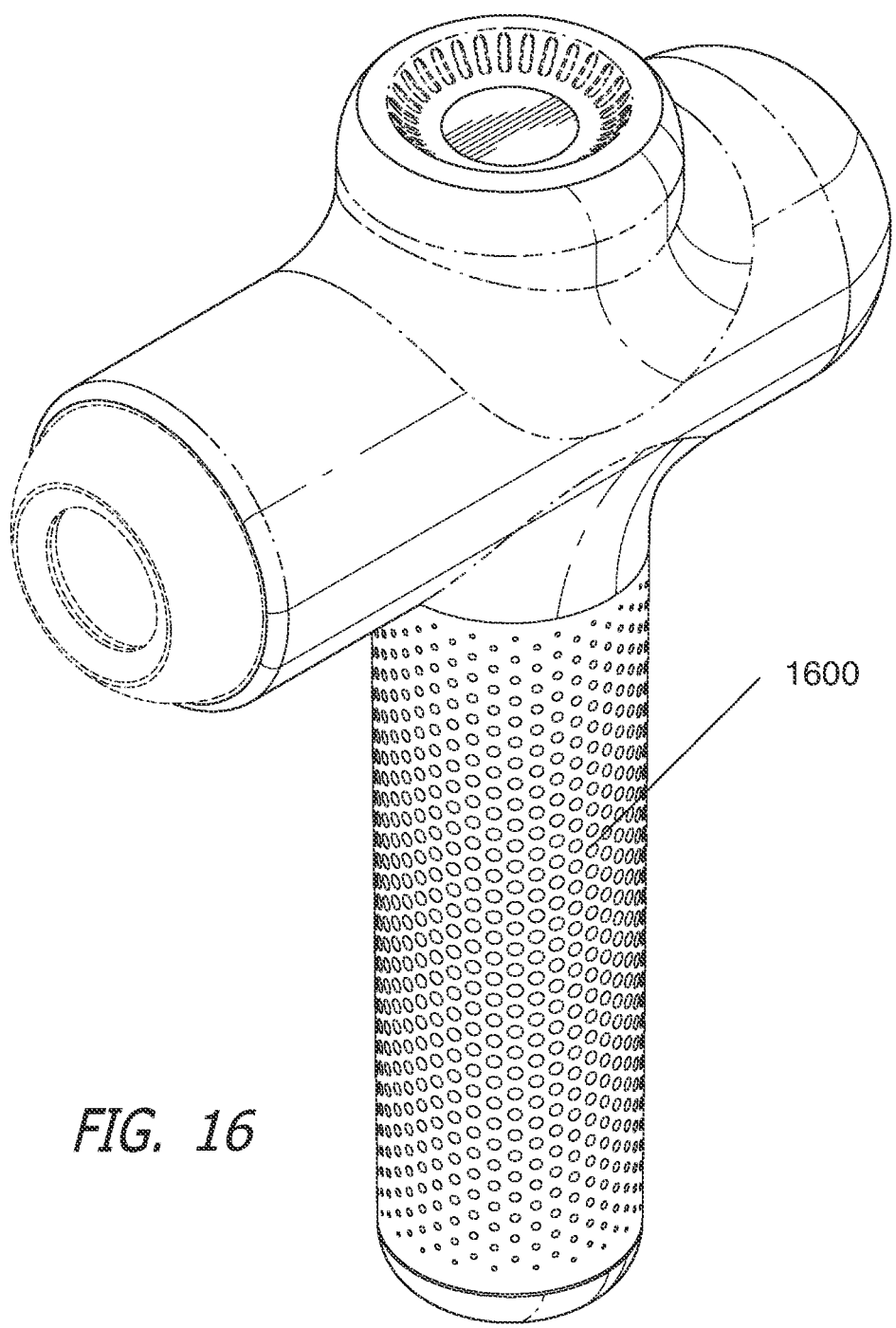
FIG. 16 illustrates a top side perspective view of a portable handheld percussion massager of the present invention having a rubber sleeve over the handle.
Figure 17:
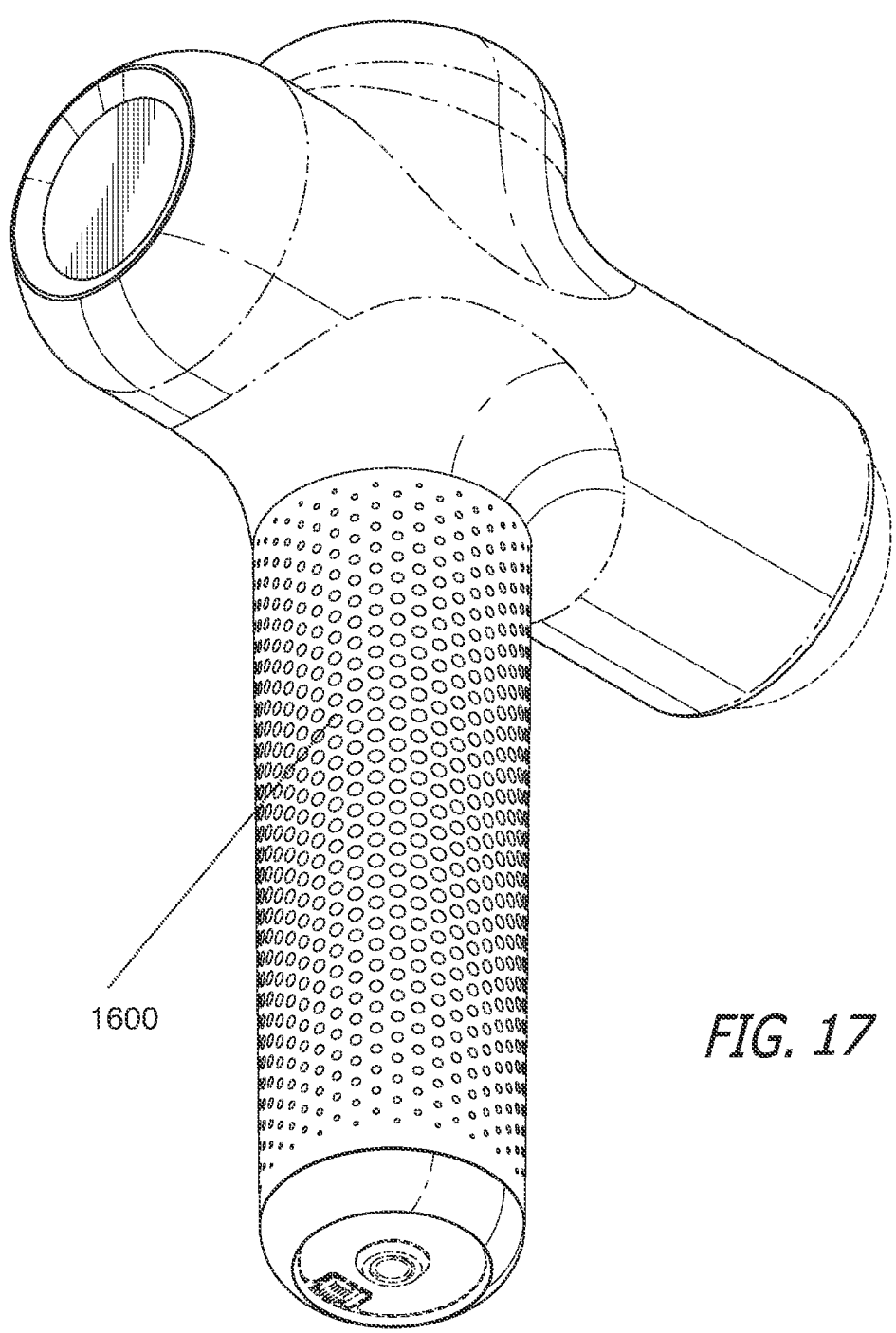
FIG. 17 illustrates a rear bottom perspective view of the portable handheld percussion massager of FIG. 16.

To increase friction and absorb vibration, the handle of the present invention may also include the incorporation of a sleeve that is made of a soft material, such as resilient gel, foam, silicon, rubber, a viscoelastic urethane polymer or rubber-like material. FIGS. 16 and 17 illustrate the use a rubber or silicon sleeve 1600 placed over the handle 710 to help protect the user's hand against vibration and/or slipping. The sleeve 1600 may also include grooves or pits to create further friction and cushioning, increasing griping ability and add air pockets to help absorb vibration. The use of both padding and air pockets can together help absorb vibration. An array of air pockets may also be included in the handle to help absorb vibration.

As described above, the temperature-controlled massage node 102, 702 of the present invention, can be affixed to a massager housing 104 or can be removable coupled to a massager housing 702. Further, many of the component parts found in the massager 100, 700, such as the battery and controller can be integrated into the massage node 102, 702 so that the massage node 102, 702 can operate independent of its connection with a massager 100, 700, especially when removably coupled. By operating independent of the massager 700, the massage node 702 can be removable coupled to other component parts, such as a handle or charger, or may be simply affixed to a handle (having little or no internal parts) for ease of use of the massage node 702 as its own self-contained massager.

FIG. 18 is a block diagram of one example of an implementation of a portable handheld massager 1800 of the present invention having the node affixed to the massager body. Here, the portable handheld massager 1800 includes both a massager housing 1804 and a massage node 1802. The massager housing 1804 includes a battery 1806, a controller 1808, a motor 1810 and a percussion massage assembly 1815. The percussion massage assembly 1815 may include a crankshaft, rod and piston for imparting percussive massage effect on the massage node 1802. Alternative, the motor 1810 may be a vibrating motor and the portable handheld massager 1800 may provide a vibrating effect on the user or the massager housing 1804 may separately include a vibrating motor in addition to the motor 1810 and percussion assembly 1815 to provide both a vibrating and/or percussive massage effect. The massager housing 1804 further includes a user control interface 1840 to allow the user to control the operation of the massager, which may include an LCD display. Optionally, the massager housing 1804 may further include a light ring or LEDs 1805 that illuminate to indicate certain operational modes of the massager 1800 or massage node 1802, as described above.

Here, the massage node 1802 includes at least one heater and/or cooler 1816, such as a Peltier plate. The massage node 1802 further includes a contact medium 1818 and temperature sensor 1830, such as a thermocouple or thermistor. The massage node 1802 may further include either or both a heat dissipating device 1814 and a fan 1820. As discussed above, the heat dissipating device 1814 may be a heat sink or the heat dissipating device 1814 form part of the node housing.

FIG. 19 is a block diagram of one example of an implementation of a portable handheld percussion massager 1900 of the present invention having the node 1902 removably coupled to the massager housing or body 1904. Here, the portable handheld massager 1900 includes both a massager housing 1904 and a massage node 1902; however, the massage node 1902 is removably coupled or attached to the massager housing 1904. Both the massager housing 1904 and massage node 1902 including electrical contacts 1934 and 1932 that make electrical contact with one another when the massage node 1902 is attached to the massager housing 1904. When the massage node 1902 is coupled to the massager housing 1904, the electrical contacts are aligned with one another, in contact with one another and/or paired with one another (when applicable) to couple the electrical contacts.

Like with the massager in FIG. 18, the massager housing 1904 includes a battery 1906, a controller 1908, a motor 1910 and a percussion massage assembly 1915. The percussion massage assembly 1915 may include a crankshaft, rod and piston for imparting percussive massage effect on the massage node 1902. Alternatively, the motor 1910 may be a vibrating motor and the massager housing 1904 may provide a vibrating effect on the user or, the massager housing 1904 may separately include a vibrating motor in addition to the motor 1910 and percussion assembly 1815 to provide both a vibrating and/or percussive massage effect. The massager housing 1904 further includes a user control interface 1940, which may include an LCD display. The massager housing 1904 may further include a light ring or LEDs 1905 that illuminates to indicate certain operational modes of the massager 1900 or massage node 1902, as described above.

Again, like in FIG. 18, the massage node 1902 includes at least one heater and/or cooler 1916, contact medium 1918 and temperature sensor 1930. The massage node 1802 may further include either or both a heat dissipating device 1914 and a fan 1920, where the heat dissipating device 1814 may be a heat sink or may be incorporated into the node housing. The massage node 1902 may also includes a separate PCB/controller or IC 1950 to assist with parsing signal information, which can help reduce the required number of electrical contacts 1932 and 1934.

In the examples provided in FIGS. 18 and 19, the motor 1810, 1910, and percussion massage assembly 1815, 1915 may be used with, or either replaced by, a vibrating motor to allow the massager 1800, 1900 to impart a vibrating massage effect on massage node 1802, 1902 (and thus the user), in addition to or in lieu of the percussive massage effect. The LED light ring 1805, 1905 may be incorporated into the massage node 1802, 1902 rather than on the massager housing 1804, 1904.

FIG. 20 is a block diagram of one example of an implementation of a portable handheld percussion massager of the present invention having an intelligent massage node 2002 in that the massage node 2002 includes its own controller 2008 and battery 2006. As illustrated, in this example, the massage node 2002 includes its own battery 2006, controller 2008, thermoelectric heater/cooler 2016, temperature sensor 2030 and contact medium 2018. The massage node 2002 may further include either of both a heat dissipating device 2014 or a fan 2020. A light ring 2005 may further be incorporated into the massage node 2002. The massage node 2002 may even include a vibrating motor 2010 to vibrate the massage node 2002.

The massage node 2002 may be affixed or attached to a handle 2050 for use, which may be a dummy handle, or may incorporate some or parts in the massage node 2002, like a separate battery and/or vibrating motor 2006.

The massage node 2002 may also be attached to a massager 2000 for imparting, for example, a percussion or vibrating massage effect on the massage node 2002. User controls may be built into the node or may be controlled wirelessly, in which case the massage node can include a transceiver or Bluetooth capabilities. The massage node 2002 may further include electrical contacts 2034 for communicating with a massager (either percussion or vibrating) or a handle via electrical contacts 2032, which may also include user controllers, or even with a charger 2060 for recharging the battery 2006 or powering the massage node 2002. The intelligent massage node 2002 can also be designed as a unitary handheld device.

In all the above examples, the power supply is shown as a battery; however, the use of a battery, although preferred, is optional. The power supply may come from either or both a battery or an electrical outlet, such that the power supply or electricity can be drawn from either or both the battery or an electrical outlet by plugging the massager housing, handle or massage node into an electrical outlet. Plugging into an outlet may also serve to charge the internal battery and/or provide power to the device.

In operation, in any of the examples described above, the massager controls include either or both heat and/or cooling effect options. When activated, a voltage is applied across joined conductors on at least one thermoelectric heater/cooler (e.g., Peltier plate) to create an electric current. When the current flows through the junctions of the two conductors, heat is removed at one junction and surface cooling occurs. At the other junction surface, heat is deposited. In other words, a first side of the plate is cooled while the second side is heated. When the current flow is reversed, the first side of the plate is heated while the second side is cooled, allowing for the Peltier plate to provide both heating and cooling effects on a first side of the plate, which effects can then be transferred to the user. The amount of voltage supplied to the Peltier plate will dictate how hot or cold the plate will be become. In certain embodiments, one temperate for both hot and cold effects can be provided, whereas in other examples, the user may select between different temperature modes (e.g., high, low and medium) and the massager can be programmed to provide different voltages to the Peltier plate in response to the user selection, thereby causing varying temperatures in the Peltier plate based upon user selection. In some examples, single, dual or triple settings for both hot and cold can be provided to a user that correspond to preset temperatures and/or supplied voltage amounts to the Peltier plate.

The massager may also include temperature sensors, which may, for example, be a thermocouple or thermistor (NTC thermistor) to regulate the amount of heat or cold effects produced by the Peltier plate. The temperature sensor is be positioned near the thermoelectric heater/cooler to sense the temperature of the massage node near the thermoelectric heater/cooler. If the thermoelectric heater/cooler (e.g., Peltier plate) become too hot, the controller can reverse the current to cool down the plate. Further, an auto-reverse to the polarity may be used to "normalize" the temperature quickly when shutting off the heat or cold so that the node does not retain unwanted temperature. The controller may also include an auto-shut off if the Peltier plate is left on for a predetermined period, or if it reaches a certain temperature. The controller can also control the time and direction in which current is applied to the thermoelectric heater/cooler and can flip between hot and cold setting to maintain a certain predetermined or user selected temperature in response to the temperatures sensed by the temperature sensor.

In some implementations, the temperature-controlled massage node is heated or cooled to a predetermined temperature upon activation of the Peltier plate to heat or cool the node. Once activated or upon activation, in certain implementations, the user can heat and cool the Peltier plate to predetermined temperatures, for example, at least two predetermined temperatures, or in some examples, at least three predetermined temperatures, may be selected by the user.

It will be understood, and is appreciated by persons skilled in the art, that one or more processes, sub-processes, or process steps described above may be performed by hardware and/or software. If the process is performed by software, the software may reside in software memory (not shown) in a suitable electronic processing component or system. The software in software memory may include an ordered listing of executable instructions for implementing logical functions (that is, "logic" that may be implemented either in digital form such as digital circuitry or source code or in analog form such as analog circuitry or an analog source such an analog electrical, sound or video signal), and may selectively be embodied in any computer-readable medium for use by or in connection with an instruction execution system, apparatus, or device, such as a computer-based system, processor-containing system, or other system that may selectively fetch the instructions from the instruction execution system, apparatus, or device and execute the instructions. In the context of this disclosure, a "computer readable medium" is any means that may contain, store or communicate the program for use by or in connection with the instruction execution system, apparatus, or device. The computer readable medium may selectively be, for example, but is not limited to, an electronic, magnetic, optical, electromagnetic, infrared, or semiconductor system, apparatus or device. More specific examples, but nonetheless a non-exhaustive list, of computer-readable media would include the following: a portable computer diskette (magnetic), a RAM (electronic), a read-only memory "ROM" (electronic), an erasable programmable read-only memory (EPROM or Flash memory) (electronic) and a portable compact disc read-only memory "CDROM" (optical). Note that the computer-readable medium may even be paper or another suitable medium upon which the program is printed, as the program can be electronically captured, via for instance optical scanning of the paper or other medium, then compiled, interpreted or otherwise processed in a suitable manner if necessary, and then stored in a computer memory.

It will be understood that the term "in signal communication" as used herein means that two or more systems, devices, components, modules, or sub-modules are capable of communicating with each other via signals that travel over some type of signal path. The signals may be communication, power, data, or energy signals, which may communicate information, power, or energy from a first system, device, component, module, or sub-module to a second system, device, component, module, or sub-module along a signal path between the first and second system, device, component, module, or sub-module. The signal paths may include physical, electrical, magnetic, electromagnetic, electrochemical, optical, wired, or wireless connections. The signal paths may also include additional systems, devices, components, modules, or sub-modules between the first and second system, device, component, module, or sub-module.

More generally, terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components The foregoing description of an implementation has been presented for purposes of illustration and description. It is not exhaustive and does not limit the claimed inventions to the precise form disclosed. Modifications and variations are possible in light of the above description or may be acquired from practicing the invention. The claims and their equivalents define the scope of the invention.

The invention claimed is:

1. A portable percussion massager comprising:
a massager housing having a body and a handle;
a battery housed within the massager housing;
a motor positioned within the massager housing;
a percussion massage assembly having a crankshaft, a rod having a first end and second end and a piston having a first end and second end, where the crankshaft is connected to the motor and the first end of the rod is connected to the crankshaft at a point offset from the rotational axis of the crankshaft and where the first end of the piston is coupled to the second end of the rod, where a node mount having an interior is in communication with the second end of the piston, and where the percussion massage assembly is configured to percussively move the piston along a reciprocation axis relative to the massager housing in response to the operation of the motor; and
at least one temperature-controlled massage node comprising a node housing having an upper portion and lower portion, where the lower portion includes an outer sleeve and where the temperature-controlled massage node is removably coupled to the node mount by the outer sleeve frictionally fitting within the interior of the node mount, where the temperature-controlled massage node includes a Peltier plate, and where at least a first electrical contact is located on the lower portion of the node housing and at least a second electrical contact is located in the interior of the node mount, where the at least first electrical contact includes an electrical pin that makes an electrical connection to the at least second electrical contact when the lower portion is coupled to the second end of the piston.

2. The portable percussion massager of claim 1 where the outer sleeve includes grooves for frictionally fitting with corresponding grooves on the interior of the node mount.

3. The portable percussion massager of claim 2 where the at least second electrical contact includes an electrical contact plate.

4. The portable percussion massager of claim 1 where the at least second electrical contact includes a plurality of electrical contact plates.

5. The portable percussion massager of claim 1 where the temperature-controlled massage node is cooled to a predetermined temperature upon activation of the Peltier plate.

6. The portable percussion massager of claim 1 where the temperature-controlled massage node is heated to a predetermined temperature upon activation of the Peltier plate.

7. A portable percussion massager comprising:
a massager housing having a front end and rear end;
a motor positioned within the massager housing having a crankshaft and rod, where the rod is connected at a first end at a point offset from the rotational axis of the crankshaft;
a piston having a first end and second end, where the first end of the piston is coupled to a second end of the rod, where the piston percussively moves relative to the massager housing in response to the operation of the motor;
a node mount positioned on the second end of the piston;
a temperature-controlled massage node having a Peltier plate, where the temperature-controlled massage node is removably coupled to the node mount by friction fit; and
a first electrical contact on the node mount and a second electrical contact on the temperature-controlled massage node, where the first electrical contact is an electrical pin and the second electrical contact is a flat-shaped electrical contact plate, and where the electrical pin and flat-shaped electrical contact plate form an electrical connection with one another when the temperature-controlled massage node is coupled to the node mount.

8. The portable percussion massager of claim 7 where the temperature-controlled massage node is heated to a predetermined temperature upon activation of the Peltier plate.

9. The portable percussion massager device of claim 7 where the portable percussion massager, upon user activation, is capable of separately heating and separately cooling the Peltier plate to at least two predetermined temperatures.

10. The portable percussion massager of claim 7 where the temperature-controlled massage node includes at least one outer sleeve that frictionally fits within an interior of the node mount.

11. The portable percussion massager of claim 7 where the temperature-controlled massage node includes at least one sealing ring that frictionally fits within an interior of the node mount.

12. The portable percussion massager of claim 7 where the temperature-controlled massage node and motor are electrically connected to the same power source.

13. A portable percussion massager comprising:
a massager housing having a body having a front end and rear end and a handle having a longitudinal cavity;
a battery housed at least partially within a gripping portion of the longitudinal cavity of the handle;
a motor positioned within the massager housing;
a percussion massage assembly having a crankshaft, a rod having a first end and second end and a piston having a first end and second end, where the crankshaft is connected to the motor and the first end of the rod is connected to the crankshaft at a point offset from the rotational axis of the crankshaft and where the first end of the piston is coupled to the second end of the rod, where the percussion massage assembly is configured to percussively move the piston relative to the massager housing in response to the operation of the motor;
at least one temperature-controlled massage node comprising a node housing having an upper portion and lower portion, where the lower portion is removably coupled to the second end of the piston on the front end of the body, where the temperature-controlled massage node includes a Peltier plate for imparting cold on the temperature-controlled massage node, and where at least one electrical contact is located on the lower portion of the node housing and at least one electrical contact is located on the second end of the piston, where the at least one electrical contact located on the second of the piston includes an electrical contact ring, and where the at least one electrical contact located on the lower portion of the node housing includes an electrical contact ring that makes an electrical connection with the electrical contact ring located on the second end of the piston when the lower portion of the at least one temperature-controlled massage node is coupled to the second end of the piston; and a controller positioned in the massager housing in communication with the battery, the temperature-controlled massage node and the motor for providing power to the temperature-controlled massage node and the motor and for controlling the operation of the motor and the temperature-controlled massage node such that the motor and temperature-controlled massage node can operate independently of one another and simultaneously with one another.

14. The portable percussion massager of claim 13 where the motor imparts a vibrating massage effect on the temperature-controlled massage node.

15. The portable percussion massager of claim 13, where the temperature-controlled massage node is coupled to the piston for moving the temperature-controlled massage node in a percussive manner.

16. The portable percussion massager of claim 13 where the temperature-controlled massage node is removably coupled to the piston.

17. The portable percussion massager of claim 13 where the temperature-controlled massage node is heated to a predetermined temperature upon activation of the Peltier plate.

18. The portable percussion massager of claim 13 where at least one of the at least one electrical contact located on the lower portion of the node housing or at least one electrical contact located on the second end of the piston comprises of a plurality of electrical contact rings.

19. The portable percussion massager of claim 13 where an indication display including at least one LED is positioned on the rear end of the body of the massager housing.

20. The portable percussion massager of claim 13 where the portable percussion massager, upon user activation, is capable of separately heating and separately cooling the Peltier plate to at least three predetermined temperatures.

21. A portable percussion massager comprising:
a massager housing having a body and a handle, the body having a front end and rear end and the handle having a longitudinal cavity;
the handle having a grip, where a battery is housed at least partially within the grip of the handle;
a motor positioned within the massager housing;
a percussion massage assembly having a crankshaft, a rod having a first end and second end and a piston having a first end and second end, where the crankshaft is connected to the motor and the first end of the rod is connected to the crankshaft at a point offset from the rotational axis of the crankshaft and where the first end of the piston is coupled to the second end of the rod, where a node mount having an interior is positioned on the second end of the piston, and where the percussion massage assembly is configured to percussively move the piston relative to the massager housing in response to the operation of the motor;
at least one temperature-controlled massage node comprising a node housing having an upper portion and lower portion, where the lower portion includes at least one sealing ring and where the temperature-controlled massage node is removably coupled to the node mount by the sealing ring frictionally fitting within the interior of the node mount, where the temperature-controlled massage node includes a Peltier plate, and where at least a first electrical contact is located on the lower portion of the node housing and at least a second electrical contact is located on the second end of the piston, where the at least first electrical contact includes an electrical pin that makes an electrical connection to the at least second electrical contact when the lower portion of the at least one temperature-controlled massage node is coupled to the second end of the piston.

22. The portable percussion massager of claim 21 where the temperature-controlled massage node includes at least one outer sleeve that frictionally fits within the interior of the node mount.

23. The portable percussion massager of claim 21 where the Peltier plate is capable of separately heating and separately cooling the temperature-controlled massage node.

24. The portable percussion massager of claim 22 where the outer sleeve includes grooves for frictionally fitting with corresponding grooves on the interior of the node mount.

25. The portable percussion massager of claim 21 where the at least second electrical contact includes a flat-shaped electrical contact plate.

26. The portable percussion massager of claim 25 where the at least second electrical contact includes a plurality of flat-shaped electrical contact plates.

27. The portable percussion massager of claim 21 where the temperature-controlled massage node is cooled to a predetermined temperature upon activation of the Peltier plate.

28. The portable percussion massager of claim 21 where an indication display including at least one LED is positioned on the rear end of the body of the massager housing.

29. The portable percussion massager of claim 21 where the temperature-controlled massage node is heated to a predetermined temperature upon activation of the Peltier plate.

* * * * *